(12) United States Patent
Patel et al.

(10) Patent No.: US 10,980,473 B2
(45) Date of Patent: Apr. 20, 2021

(54) IDENTIFYING AND CHARACTERIZING NOCTURNAL MOTION AND STAGES OF SLEEP

(71) Applicant: Intel Corporation, Santa Clara, CA (US)

(72) Inventors: Sarin Patel, San Francisco, CA (US); Andrew A. Stirn, San Francisco, CA (US); Steven P. Szabados, San Francisco, CA (US)

(73) Assignee: Intel Corporation, Santa Clara, CA (US)

( * ) Notice: Subject to any disclaimer, the term of this patent is extended or adjusted under 35 U.S.C. 154(b) by 1132 days.

(21) Appl. No.: 15/038,195

(22) PCT Filed: Jan. 1, 2015

(86) PCT No.: PCT/US2015/010004
§ 371 (c)(1),
(2) Date: May 20, 2016

(87) PCT Pub. No.: WO2015/119726
PCT Pub. Date: Aug. 13, 2015

(65) Prior Publication Data
US 2016/0287168 A1 Oct. 6, 2016

Related U.S. Application Data

(60) Provisional application No. 61/923,212, filed on Jan. 2, 2014, provisional application No. 61/923,204, filed on Jan. 2, 2014.

(51) Int. Cl.
*A61B 5/00* (2006.01)
*A61B 5/024* (2006.01)
*A61B 5/11* (2006.01)

(52) U.S. Cl.
CPC .......... *A61B 5/4812* (2013.01); *A61B 5/0022* (2013.01); *A61B 5/02416* (2013.01);
(Continued)

(58) Field of Classification Search
CPC ... A61B 5/4812; A61B 5/4809; A61B 5/0022; A61B 5/02416; A61B 5/02405;
(Continued)

(56) References Cited

U.S. PATENT DOCUMENTS

2003/0163059 A1 8/2003 Poezevera et al.
2004/0049132 A1 3/2004 Barron et al.
(Continued)

FOREIGN PATENT DOCUMENTS

WO WO2015119726 8/2015

OTHER PUBLICATIONS

International Preliminary Report on Patentability and Written Opinion in International Application No. PCT/US2015/010004 dated Jul. 5, 2016.
(Continued)

*Primary Examiner* — Matthew Kremer
*Assistant Examiner* — Avery M Foley
(74) *Attorney, Agent, or Firm* — Patent Capital Group

(57) ABSTRACT

Disclosed herein are systems, methods and a computer readable storage medium that determine an individual's movement during sleep. In some embodiments, the identification is based on data from a motion sensor included in wearable device. In some embodiments, the individual wears the wearable device on his wrist during the individual's resting and/or sleep activities. In some embodiments, the system, methods and the computer readable storage medium automatically identify the various (stages) types of sleep during an individual's sleep periods that include periods of REM sleep, deep sleep, and light sleep and that are indicative of the individual's overall well-being and health.

18 Claims, 22 Drawing Sheets

(52) U.S. Cl.
CPC ............ *A61B 5/1118* (2013.01); *A61B 5/681* (2013.01); *A61B 5/7282* (2013.01); *A61B 5/742* (2013.01); A61B 2560/0475 (2013.01); A61B 2562/0219 (2013.01)

(58) Field of Classification Search
CPC ..... A61B 5/1118; A61B 5/681; A61B 5/7282; A61B 5/742; A61B 2560/0475; A61B 2562/0219
See application file for complete search history.

(56) References Cited

U.S. PATENT DOCUMENTS

| | | | |
|---|---|---|---|
| 2005/0177051 A1* | 8/2005 | Almen | A61B 5/02405 600/509 |
| 2008/0027331 A1 | 1/2008 | Suzuki et al. | |
| 2008/0167565 A1* | 7/2008 | Laitio | A61B 5/0205 600/513 |
| 2009/0118599 A1* | 5/2009 | Heruth | A61B 5/1116 600/301 |
| 2009/0240155 A1 | 9/2009 | Nakayama et al. | |
| 2011/0092831 A1* | 4/2011 | Herscovici-Cohen | A61B 5/1073 600/500 |
| 2015/0190086 A1* | 7/2015 | Chan | A61B 5/4812 600/301 |
| 2015/0216475 A1* | 8/2015 | Luna | A61B 5/02438 600/301 |

OTHER PUBLICATIONS

International Search Report and Written Opinion in International Application No. PCT/US2015/010004 dated Aug. 25, 2015.

* cited by examiner

IDENTIFYING AND CHARACTERIZING NOCTURNAL MOTION AND STAGES OF SLEEP

CROSS-REFERENCE TO RELATED APPLICATIONS

This application is a national stage application under 35 U.S.C. § 371 of PCT International Application Serial No. PCT/US2015/010004, filed on Jan. 1, 2015 and entitled "Identifying And Characterizing Nocturnal Motion And Stages Of Sleep", which application claims the benefit of U.S. Provisional Application Nos. 61/923,212, filed Jan. 2, 2014, and entitled "Identifying Stages of Sleep", and 61/923,204, filed on Jan. 2, 2014, and entitled "Identifying and Characterizing Nocturnal Motion" both of which are considered part of and are hereby incorporated by reference in their entirely in the disclosure of this application.

BACKGROUND

The present disclosure generally relates to identifying nocturnal movements and sleep stages of a user who is wearing a device during sleep. Current wearable devices provide minimal information about a user's sleep. However, since an individual's sleep pattern directly correlates with his overall well-being and health, it would be useful to obtain additional sleep information and data. This includes, for example, the amount of an individual's rapid eye movement (REM) sleep, light sleep, and deep sleep. Additional sleep information includes an individual's movements and activities during sleep, the individual's turning and twisting or periodic movement of his limb as it relates to a person's periodic limb movement disorder.

SUMMARY

Systems, methods and a computer readable storage medium are disclosed to determine an individual's movement during sleep. In some embodiments, the identification is based on data from a motion sensor included in wearable device. In some embodiments, the individual wears the wearable device on his wrist during the individual's resting and/or sleep activities. In some embodiments, the system, methods and the computer readable storage medium automatically identify the various stages (types) of sleep during an individual's sleep periods that include periods of REM sleep, deep sleep, and light sleep. Characterizing sleep is useful, because sleep is important to the user's health and well-being, and sleep behaviors are indicative of a person's health.

The method for identifying rapid eye movement (REM) sleep comprises receiving heart rate data associated with a sleeping user at a plurality of time points, identifying a time domain characteristic of the heart rate data, and determining a presence of REM sleep based on the identified time domain characteristics of the heart rate data.

The method for identifying deep sleep comprises receiving heart rate data and motion data associated with a sleeping user at a plurality of time points identifying a time domain characteristic of the heart rate data in a time domain, identifying motion activity by the user, and determining a presence or absence of deep sleep based on the identified time domain characteristics and the identified motion activity.

The method for characterizing nocturnal motion comprises receiving motion data associated with a sleeping user at a plurality of time points, identifying motions of a magnitude larger than a threshold, and storing the identified motions. S

BRIEF DESCRIPTION OF THE SEVERAL VIEWS OF THE DRAWINGS

The disclosed embodiments have other advantages and features which will be more readily apparent from the detailed description, the appended claims, and the accompanying figures (or drawings). A brief introduction of the figures is below.

The Figures (FIGS.) and the following description relate to preferred embodiments by way of illustration only. It should be noted that from the following discussion, alternative embodiments of the structures and methods disclosed herein will be readily recognized as viable alternatives that may be employed without departing from the principles of what is claimed.

DETAILED DESCRIPTION

Terms used in the claims and specification are defined as set forth below less otherwise specified.

One embodiment of a disclosed system, method and computer readable storage medium determines a user's movement during sleep. In some embodiments, the identification is made based on data from a motion sensor. One embodiment of a disclosed system, method and computer readable storage medium automatically identifies the various types of sleep of a user's period of sleep. For example, periods of REM, deep sleep, and light sleep are identified. Characterizing sleep is useful because sleep is important to health. Sleep behaviors are indicative of a person's health. Quality of sleep is relevant to a person's performance awake and thus providing information about sleep is useful for users who wish to optimize their health and overall well-being.

Reference will now be made in detail to several embodiments, examples of which are illustrated in the accompanying figures. It is noted that wherever practicable similar or like reference numbers may be used in the figures and may indicate similar or like functionality. The figures depict embodiments of the disclosed system (or method) for purposes of illustration only. One skilled in the art will readily recognize from the following description that alternative embodiments of the structures and methods illustrated herein may be employed without departing from the principles described herein.

Example Device Configuration

Figure 1:
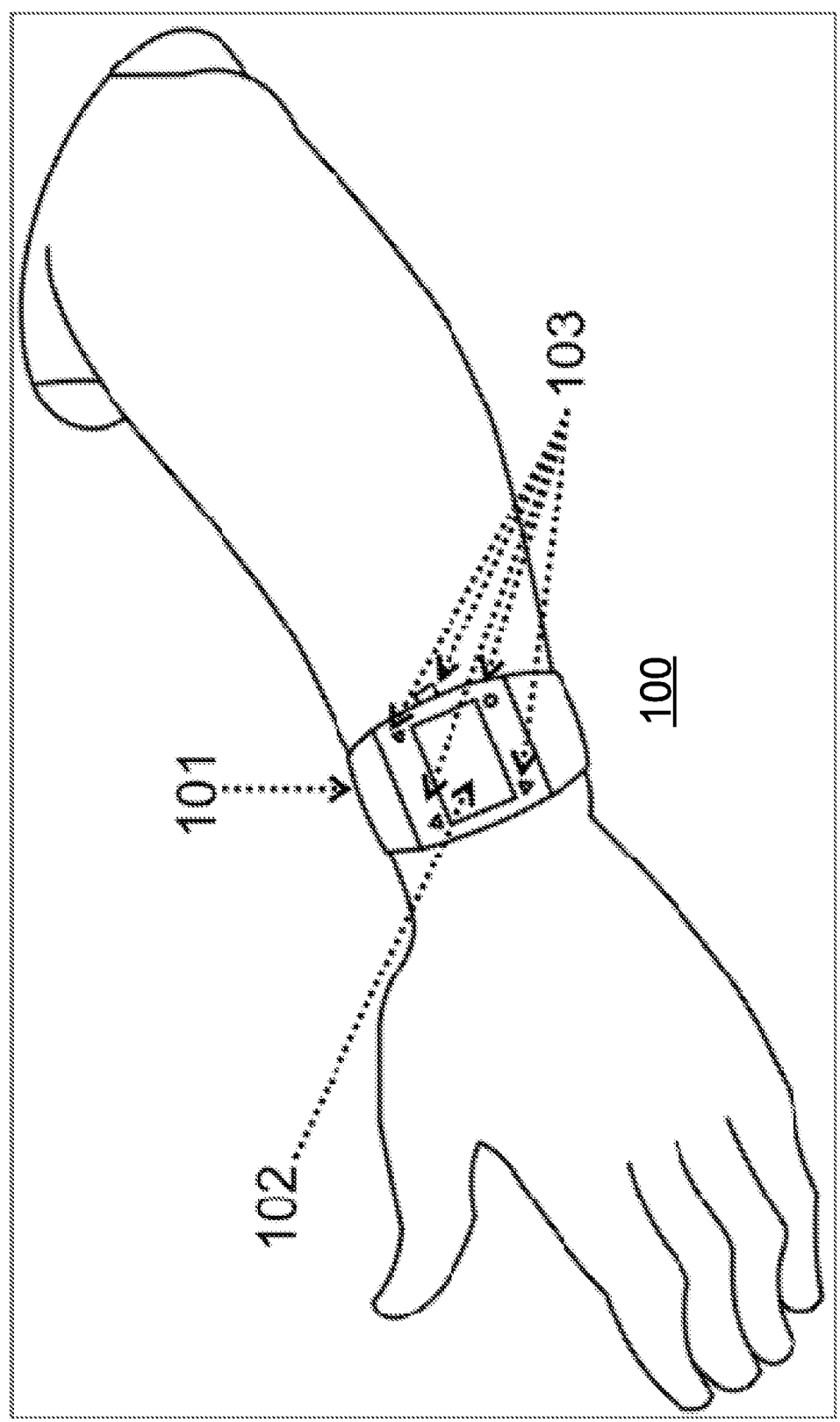
FIG. 1 illustrates a wearable device with a display, according to some embodiments.

FIG. 1 illustrates a wearable device 100, according to some embodiments. The exemplary device 100 is worn on the wrist attached through a fastening system 101. The fastening system 101 may be removable, exchangeable or customizable. The device 100 includes a display 102 and user interaction points 103. In some embodiments, the wearable device is configured to be worn by the user while the user is resting and/or sleeps, continuously monitoring heart rate and activity levels of the user. The device measures the user's heart rate recovery automatically, without explicit input from the user. Because the device is configured to be worn throughout daily activities, the device measures a user's heart rate recovery on a regular basis to monitor the user's physical condition and provide regular feedback as to the user's cardiovascular health.

The wearable device 100 is configured to be in close proximity to or in contact with a user. For example, the device 100 may be worn on a user's appendage or portion thereof, e.g., an arm or a wrist. As another example, the device 100 may be worn on a user's chest. A fastening system 101 configured to fasten the device 100 to a user's appendage is shown, although the device may alternatively be portable rather than worn. For example, one or more components of the device 100 may be carried in a pocket of a worn garment or affixed to a bag strap or belt. The fastening elements 101 may be removable, exchangeable, or customizable. Furthermore, although embodiments are described herein with respect to a wrist-worn device, other form factors or designed wear locations of the wearable device 100 may alternatively be used. For example, embodiments of the method described herein may be implemented in arm-worn devices, head-worn devices, chest-worn devices, clip-on devices, and so forth. In some embodiments, components of the device 100 described herein are components of two or more devices, rather than enclosed within a single device. That is, one or more of the data collection, processing, and display functions described herein may be performed by a device remote from the user. In this case, the separate components of the device 100 are communicatively coupled by wired or wireless communication, continuously communicating data between the components or transferring data at specified times. For example, a wearable component of the device 100 may continuously communicate data to an external device (e.g. a smartphone), which processes the data. As another example, a user may periodically connect a wearable component of the device 100 to an external computing device, such as a user's computer or a remote server, to transfer data collected by the wearable component to the external computer.

The wearable device 100 includes a display (or screen) 102 and several user interaction points 103. The display 102 and user interaction points 103 may be separate components of the device 100, or may be a single component. For example, the display 102 may be a touch-sensitive display configured to receive user touch inputs and display information to the user. The wearable device may also have a display element such as 102 without interaction points, or interaction points 103 without a display element such as 102.

It should be noted that the device 100 may include additional components not shown in FIG. 1. In particular, the device 100 includes one or more sensors for monitoring various physiological or kinematic parameters of the user of the device 100.

Figure 2:
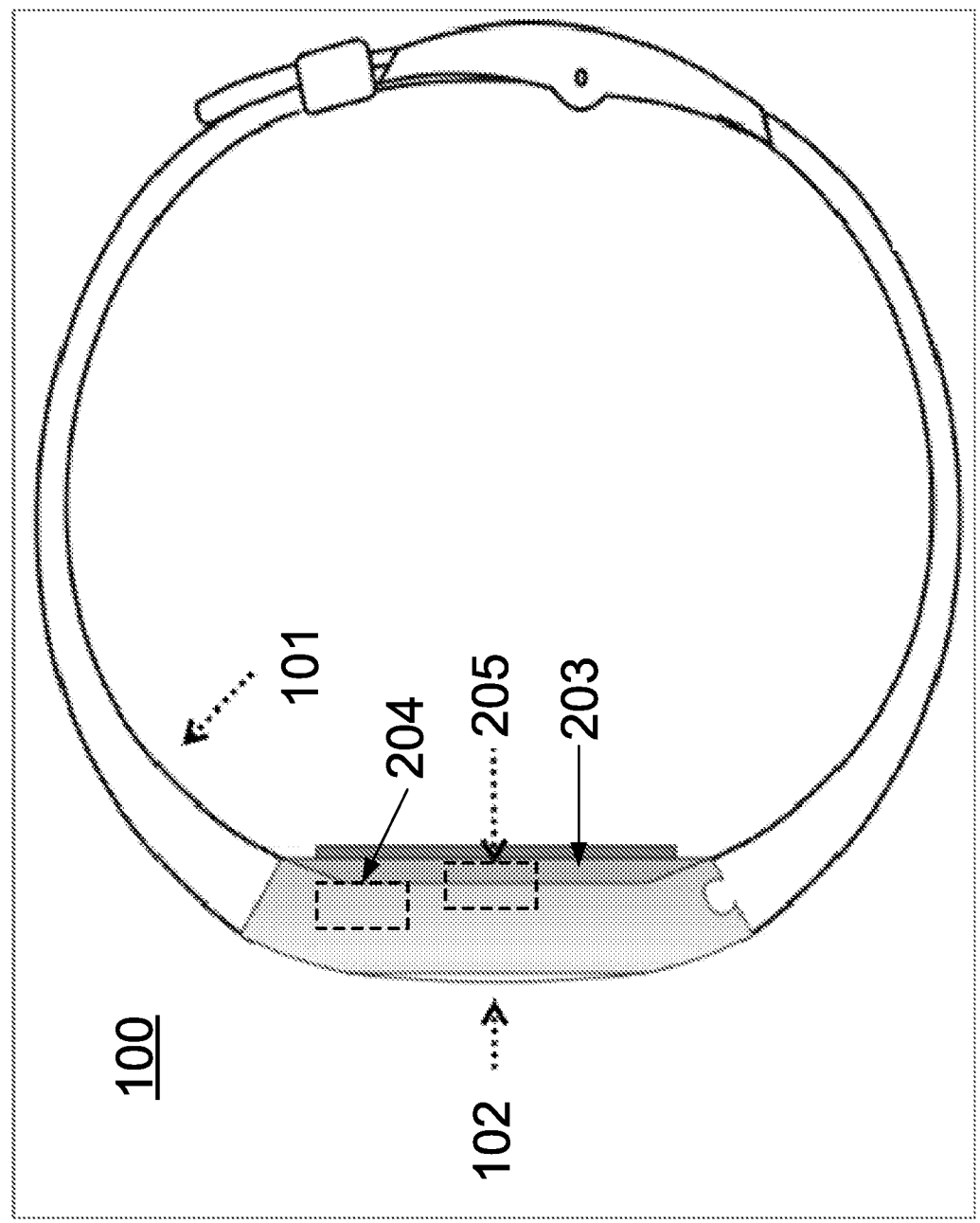
FIG. 2 illustrates a side view of a wearable device, according to some embodiments.

FIG. 2 illustrates a side view of the wearable device 100, according to some embodiments. The side view shows the fastening system 101, a display (or screen) 102, and one or more processors 203. Although not shown, the device 100 may include a display driver. In addition, the device 100 may include a memory (e.g., a random access memory (RAM) and/or read only memory (ROM)) and/or memory cache as well as a non-transitory storage medium (e.g., a flash memory). The processor 203, drivers, memories, storage medium, and sensors (further described below) may be communicatively coupled through a data bus as described in inure detail with regard to FIG. 19. Additionally, an optical sensing system 205 and a motion system 204 are illustrated.

The processor 203 receives data from a motion system 204 and an optical sensing system 205. Using the data received from both systems, the processor 203 determines the heart rate and characteristics of the heart rate of the user. In one embodiment, the processor 203 analyzes the data from the optical sensing system 205 to determine the user's heart rate at periodic intervals, e.g., every ten seconds. Using motion data received from the motion system 204, the processor 203 derives various parameters relating to the motion of the user, such as patterns in the user's movements and magnitude, frequency, and duration of the movements. The motion data is used to determine an activity level of the user, which quantifies intensity of an activity based on the detected magnitude and duration. In some embodiments, the processor 203 is configured to identify a type of sleep activity in which the user is engaged based on the data received from the motion system 204. For example, the processor 203 identifies if a user suffers from periodic limb movement disorder based on patterns in the user's movement derived from the motion data. In some embodiments, the processor 203 is configured to modify the device 100 based on the detected activity.

It is noted that the algorithms, i.e. methods and processes, described herein are embodied as instructions that are stored within the storage medium and/or ROM, are loadable into the memory (e.g., RAM), and are executable by the processor 203. It is further noted that the processes can be embodied as instructions that are stored within the storage medium and/or ROM, are loadable into the memory (e.g., RAM), and are executable by the processor 203.

The motion system 204 comprises a motion sensor. Example of motion sensors include, but are not limited to, a magnetometer, an accelerometer, a gyroscope, and a pressure sensor. In some embodiments, the motion system 204 includes multiple types of motion sensors. In some embodiments, the motion system 204 includes a single motion sensor. The motion sensor detects motion of the user of the device 100 by measuring rotational acceleration, motion, position, and/or changes in rectilinear or rotational speed of the device 100, which is one means for performing the function of detecting motion. In some embodiments, the motion sensor is an accelerometer measuring acceleration of the device 100 in one or more axes. Motion data from the motion system 204 can comprise data for motion in multiple dimensions (e.g., 2-dimensional (x- and y-direction) or 3-dimensional (x- and y-direction and, e.g., time)) as determined by an accelerometer.

In some embodiments, the motion sensor includes a gyroscope monitoring the orientation of the device 100 and/or the orientation or activity of the user. In some embodiments, a magnetometer is included to calibrate the gyroscope or to provide direction-based functionality, which is one means for performing this function. Some embodiments of the motion sensor include both an accelerometer and a gyroscope, or an accelerometer, gyroscope, and magnetometer.

In some embodiments, the motion data is acquired periodically, for example every second, 64 times every second, 128 times every second, every 15 seconds, every 30 seconds, every 45 seconds, every 60 seconds, every 75 seconds, every 90 seconds, etc. In some embodiments, data is collected at one frequency and then averaged to provide a single data point spanning a larger time period. For example, data collected every second can be averaged to provide a single data point for each minute.

Figure 3:
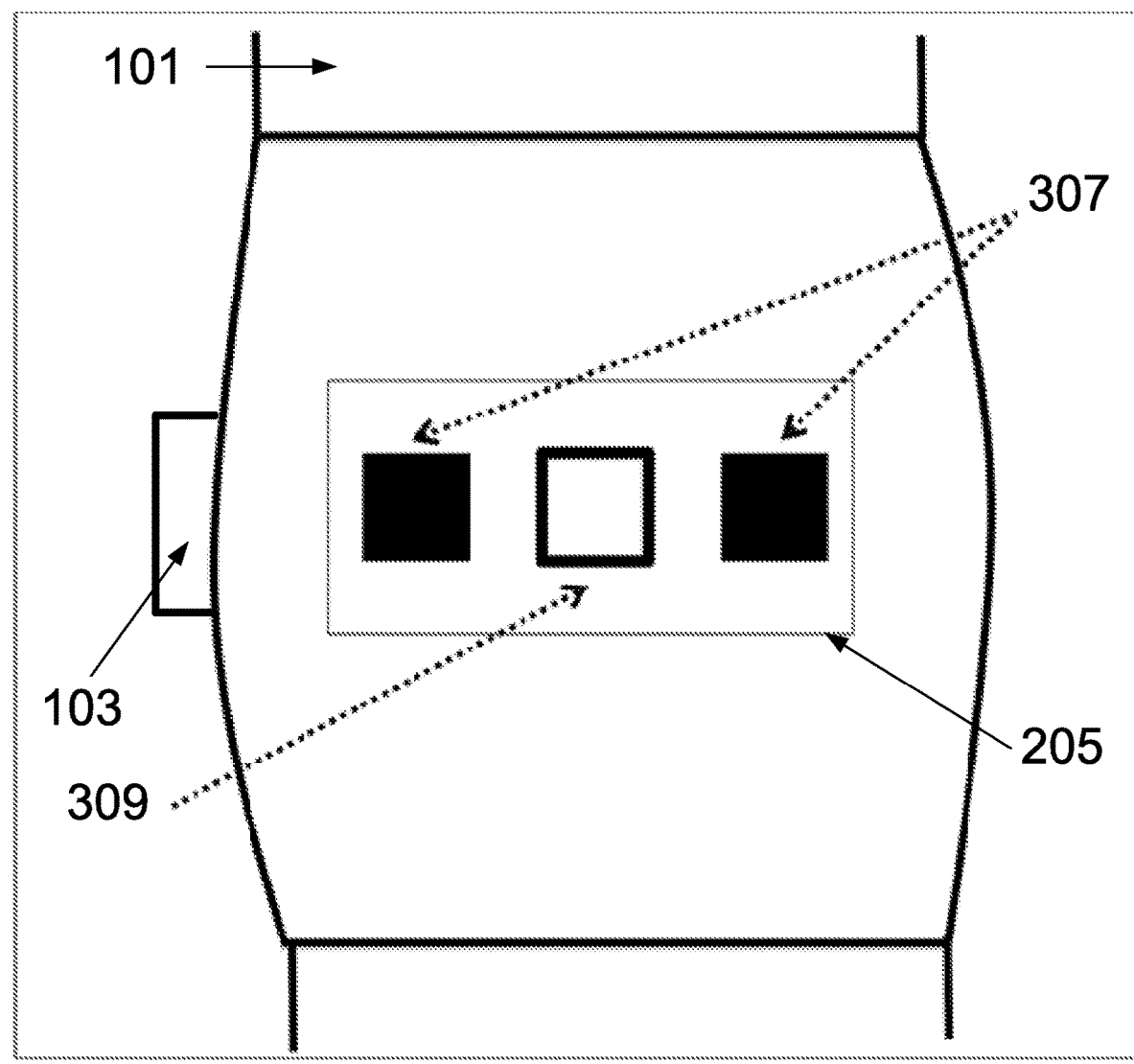
FIG. 3 illustrates a cross-sectional view of a wearable device including an optical sensing system, according to some embodiments.

FIG. 3 illustrates a cross-sectional view of a wearable device including an optical sensing system 205, according to some embodiments. The optical sensing system 205 comprises one or more optical sensors 309 and optionally one or more optical emitters 307. Some embodiments include one optical sensor 309 and two optical emitters 307. In some embodiments, the device 100 includes additional sensors, e.g., electrodermal activity (EDA) sensors, skin conductance or sweat sensors, temperature sensors, humidity sensors, and/or hydration sensors. Signals from the optical sensor 309 are processed to identify heart rate and characteristics of the heart rate, Optical emitter 307 includes a light emitting diode (LED) and lasers. In some embodiments light emitted from the optical emitter 307 is in the visible yellow and green ranges (500 nm to 600 nm). In some embodiments, light in the visible spectrum, such as blue and red, or the infrared spectrum may be used instead of or in addition to green light. In some embodiments, the optical emitter 307 emits light in other wavelengths in addition to those used for identifying blood flow features. For example, emitted light may be full spectrum white light.

In some embodiments that include more than one optical emitter, the optical emitters 307 emit light at the same time. In some embodiment, the optical emitters 307 emit light in an alternating fashion. In some embodiment, the optical emitters 307 are set to emit light independently at some times and simultaneously at others. The optical sensor 309 detects light in the wavelengths of light emitted by the optical emitter 307. An example of an optical sensor 309 is a Light-To-Voltage (LTV) sensor, including, but not limited to, a Taos TSL13T or the like.

Light is emitted from the optical emitter 307. An optical signal is acquired via the optical sensor 309. In some embodiments, the emission of light and subsequent collection of signals occurs continuously or continually while the device is worn by the user. Continually refers to repeatedly and not requiring an uninterrupted period of time. Whether the device is being worn can be assessed through any means known to a person skilled in the art, including, but not limited to, for example the use of a proximity sensor, which is one means for performing this function. In some embodiments, the optical sensing system 205 is not continuously active. In some embodiments, the optical sensing system 205 generates data at intervals (continually and non-continually). The intervals may be regular or irregular.

Figure 4:
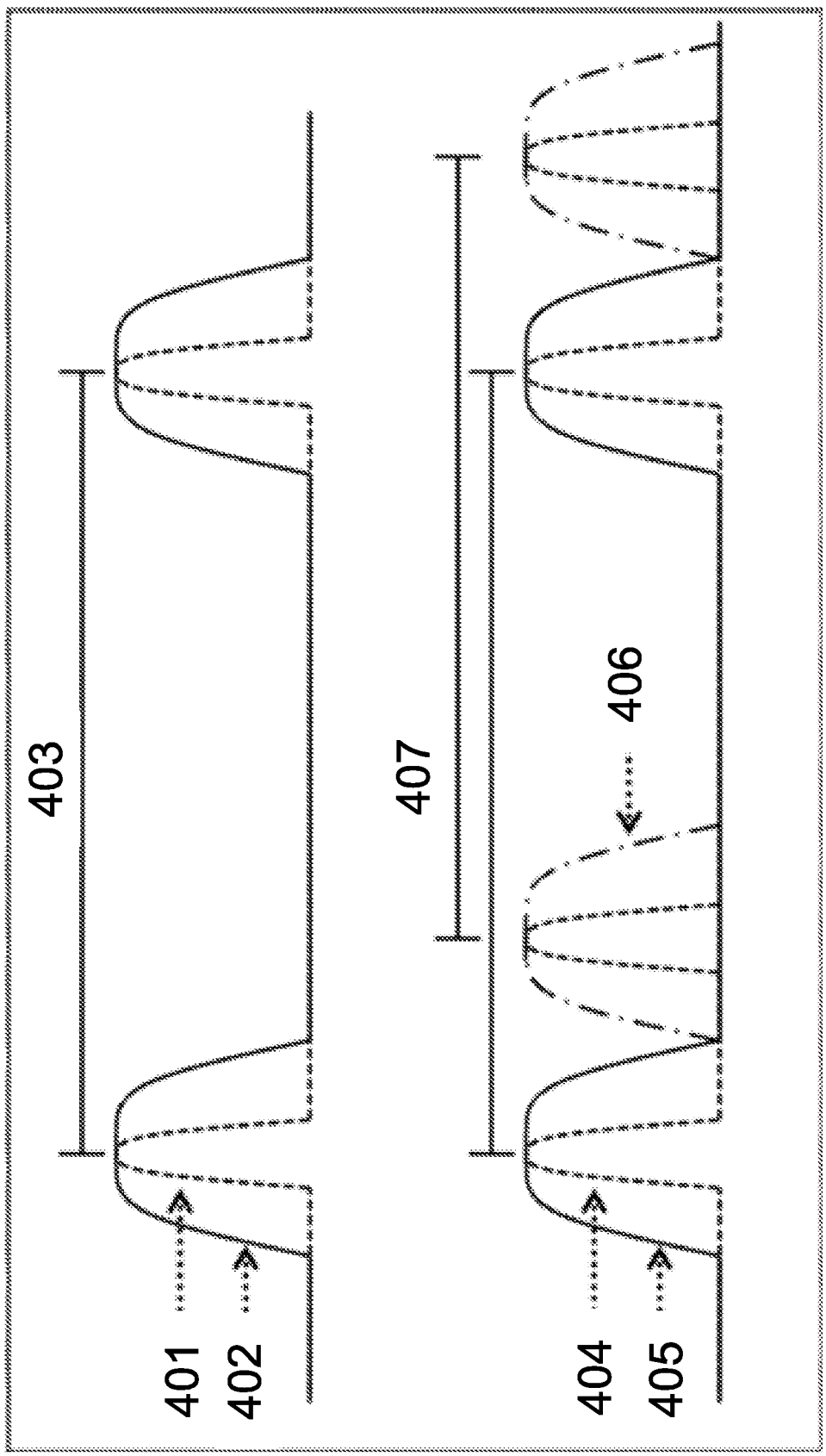
FIG. 4 illustrates a signal acquisition schema of an optical sensing system, according to some embodiments.

FIG. 4 illustrates an example of light emission and sensor sampling schemes, according to some embodiments. In a first embodiment, shown in the top graph, both optical emitters 307 emit light onto the skin at the same time. Line 401 illustrates activity of the optical sensor 309 and line 402 illustrates activity of the optical emitters 307. In each case the line illustrates when the respective component is on and off. Line 403 illustrates the sampling rate. In some embodiments, the sampling frequency lies within the following ranges: 2 Hz-4096 Hz, 20 Hz-1024 Hz, 30 Hz-1000 Hz, 50 Hz-512 Hz, 64 Hz-512 Hz, 100 Hz-256 Hz or 128 Hz-200 Hz. In some embodiments the sampling frequency is 20, 30, 32, 50, 64, 100, 128, 200, 256, 500, 512, 1000 or 1024 H.

In a second embodiment illustrated the bottom graph of FIG. 4, the optical emitters 307 emit light onto the skin at different times in an alternating fashion. Line 404 illustrates activity of the optical sensor 309 and lines 405 and 406 each illustrate activity of one of the optical emitters 307. In each case the line illustrates when the respective component is on and off. Lines 407 illustrate the sampling rate. In some embodiments the sampling frequency for each of the optical emitters 307 is between 2 Hz-4096 Hz, 20 Hz-1024 Hz, 30 Hz-1000 Hz, 50 Hz-512 Hz, 64 Hz-512 Hz, 100 Hz-256 Hz or 128 Hz-200 Hz. In some embodiments the sampling frequency is 20, 30, 32, 50, 64, 100, 128, 200, 256, 500, 512, 1000 or 1024 Hz. In other embodiments, a combination of the two sampling schemes is utilized.

Figure 5:
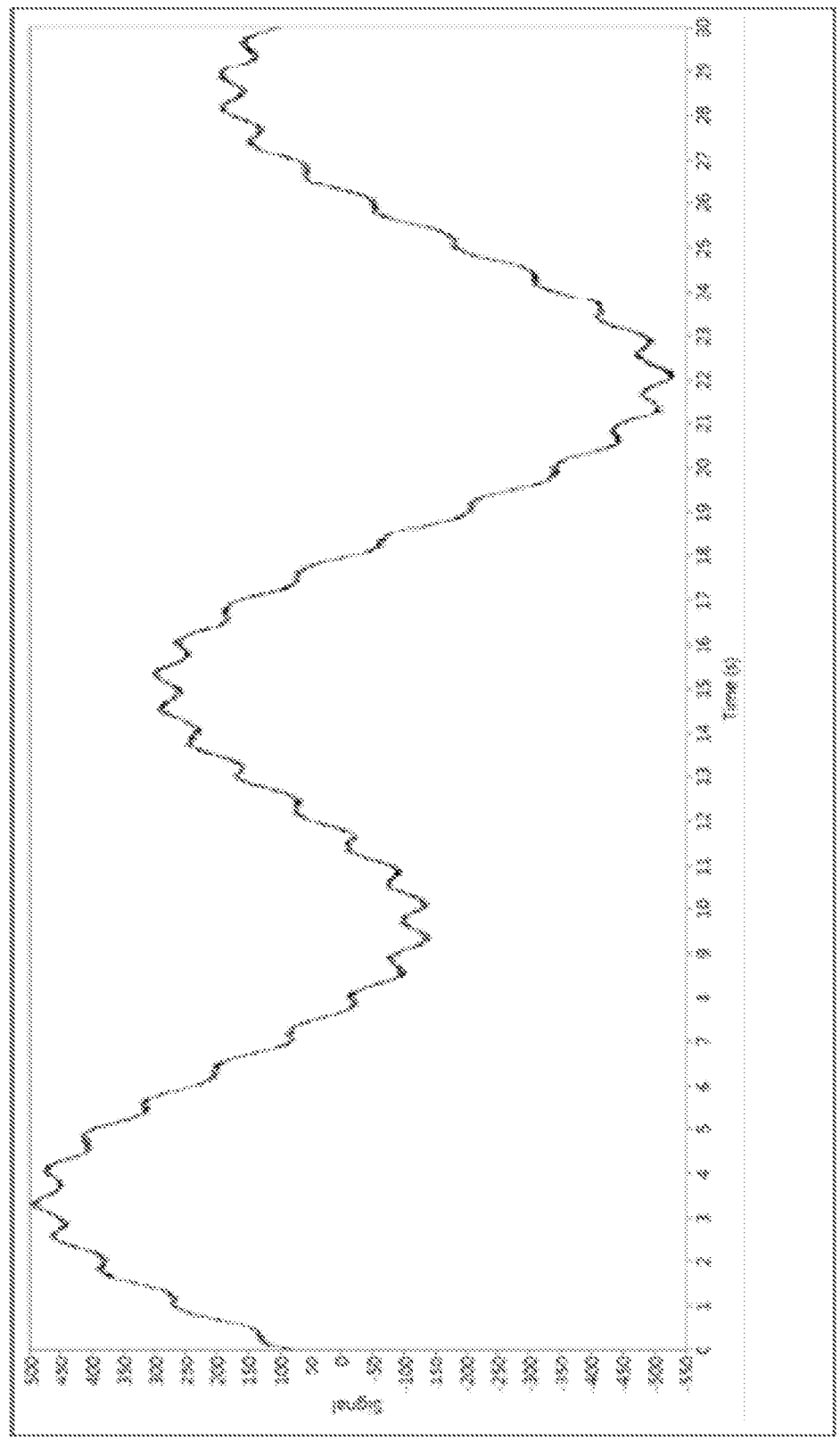
FIG. 5 illustrates a raw signal acquired from an optical sensing system, according some embodiments.

FIG. 5 illustrates an example of an acquired optical signal, according to some embodiments. The signal has several main constituents—a large, low frequency signal, a smaller, higher frequency signal and still smaller signal representing noise.

Identification of Body Movement

Figure 6:
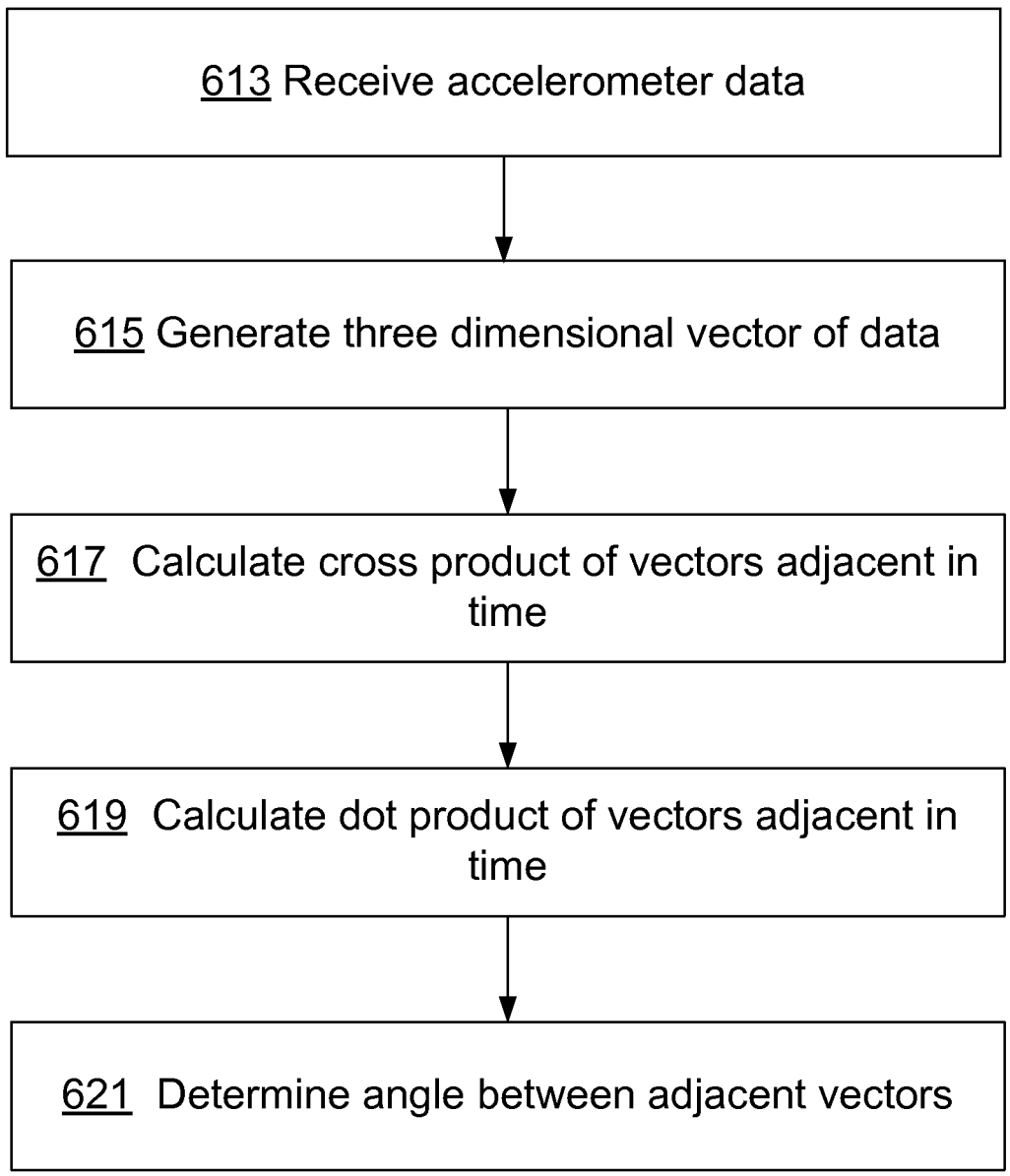
FIG. 6 illustrates a flow chart for a method for identifying and characterizing nocturnal motion, according to some embodiments.
Figure 7:
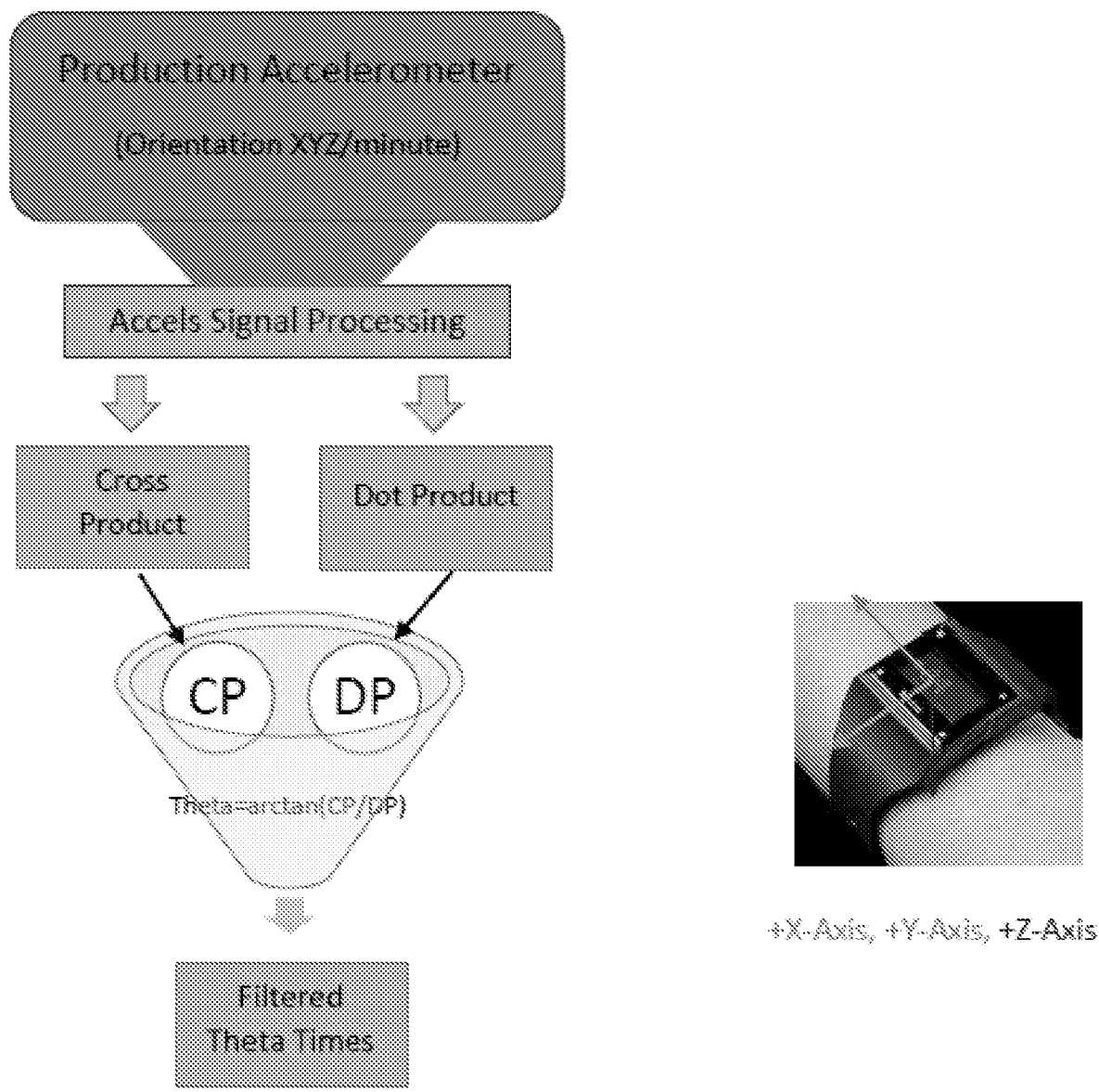
FIG. 7 illustrates a flow chart for a method for identifying and characterizing nocturnal motion, according to some embodiments.
Figure 8A:
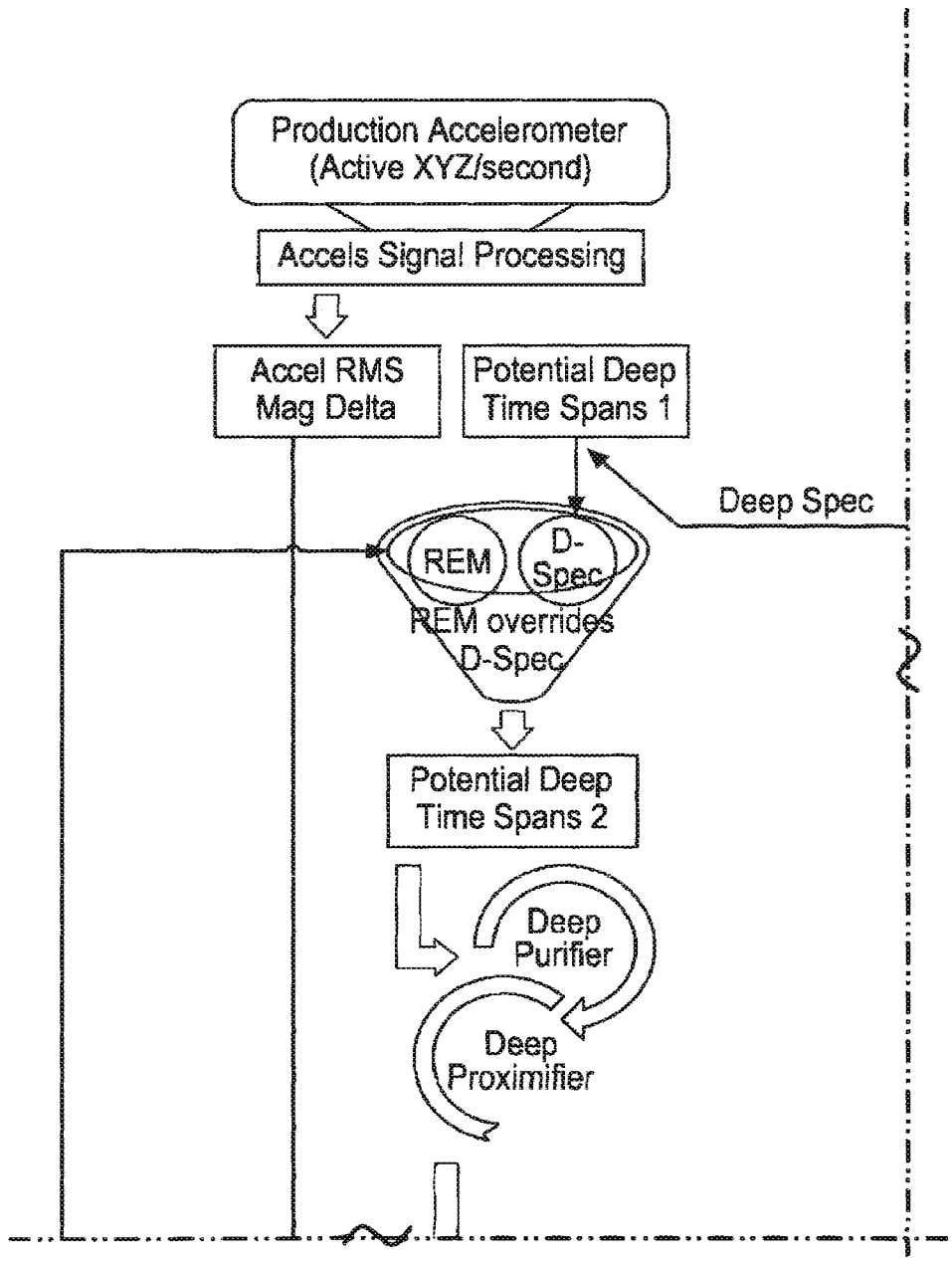
FIGS. 8A-8D illustrate a flow chart of a method of identifying and characterizing deep sleep, light sleep, and REM sleep, according to some embodiments.
Figure 8B:
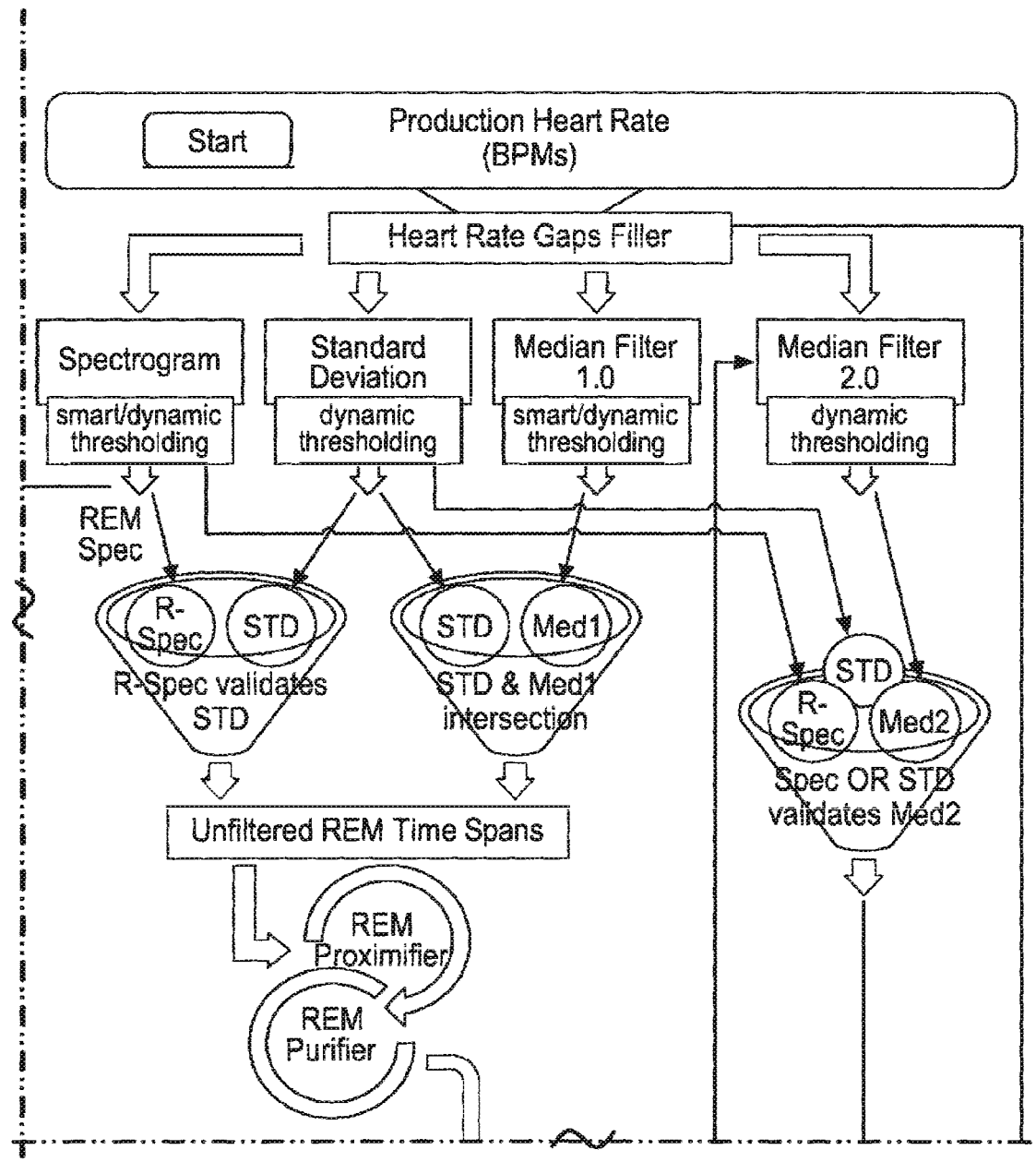
Figure 8C:
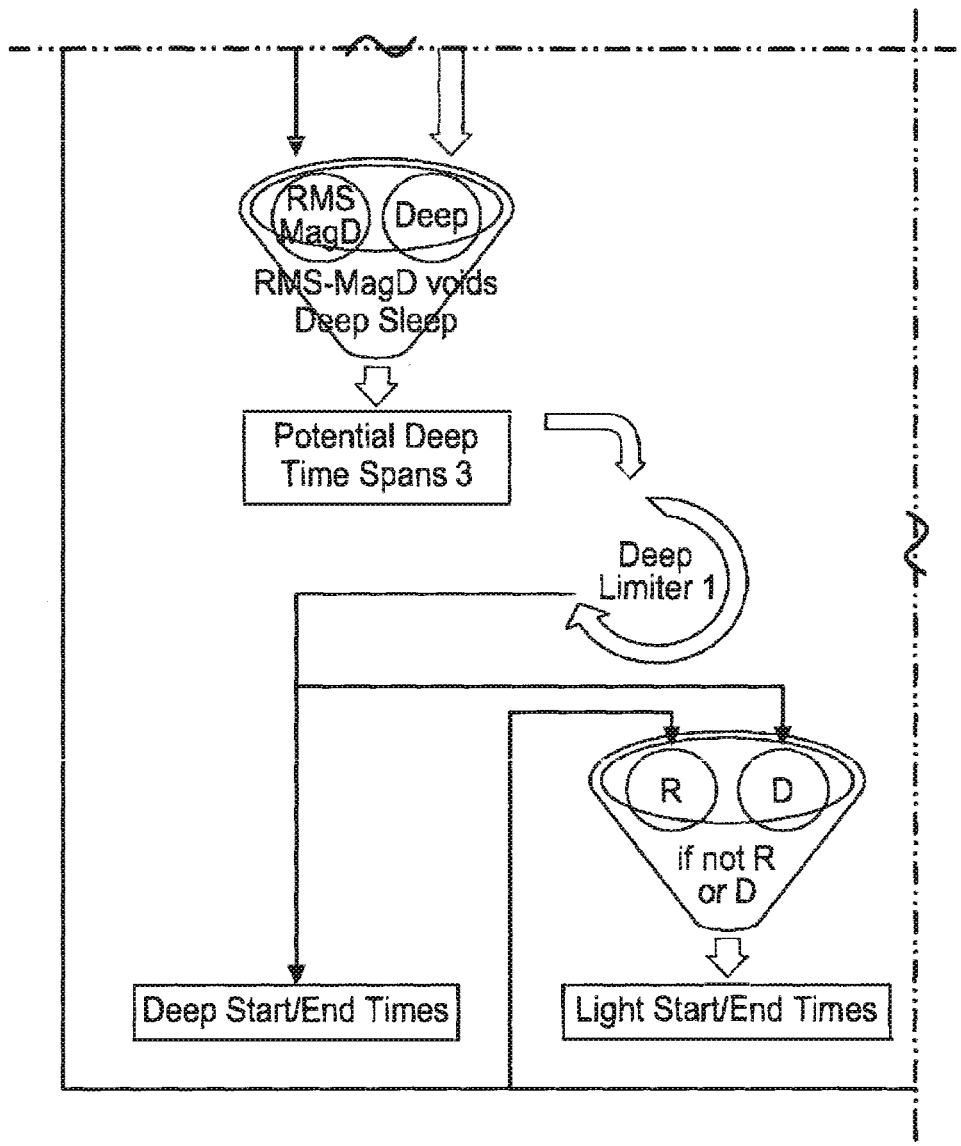
Figure 8D:
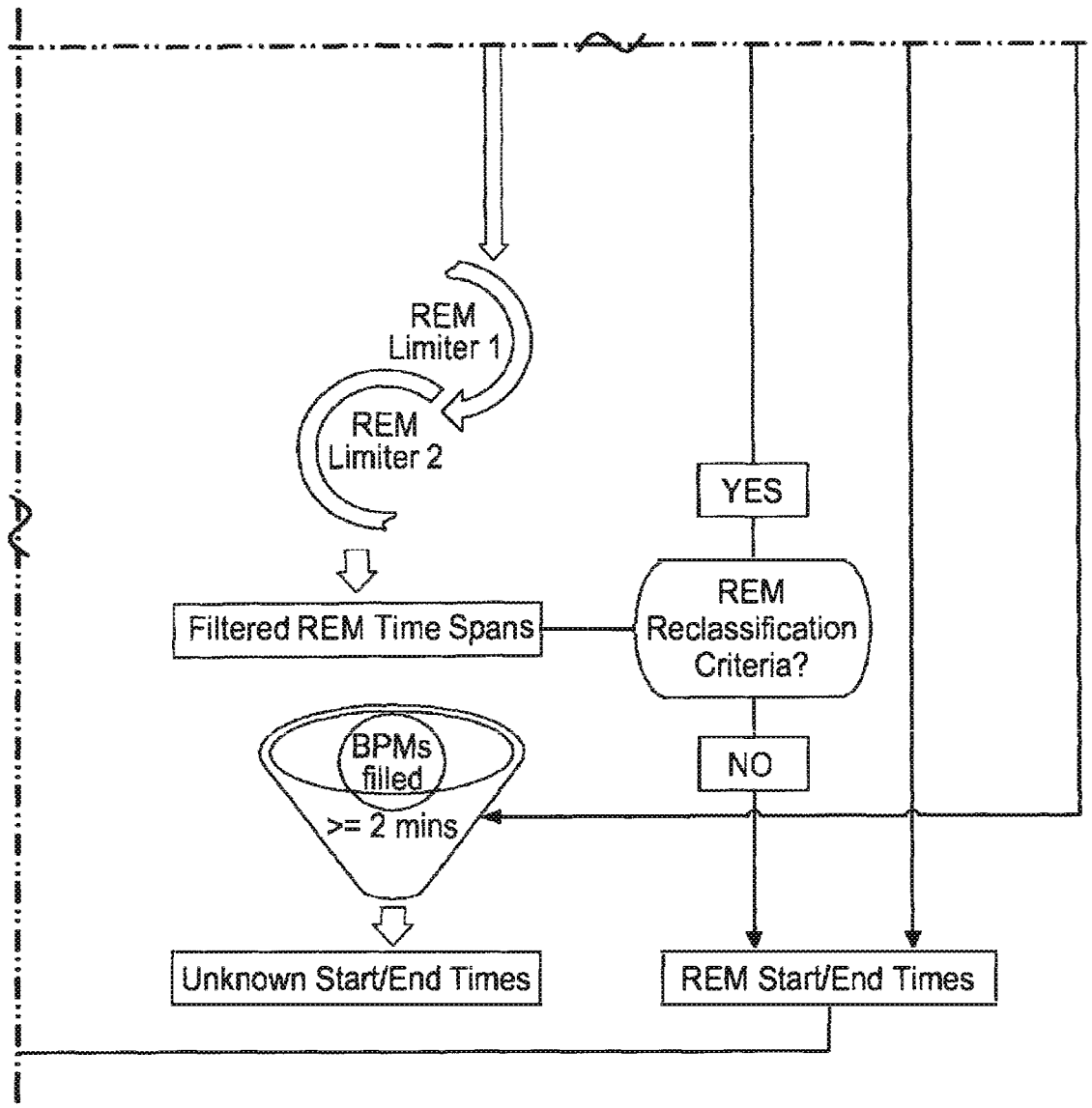

FIGS. 6 and 7 illustrate methods for the identification and characterization of nocturnal motion, according some embodiments. In some embodiments, the method identifies changes in position of the body part upon which the device 100 is affixed (e.g., the wrist) that are substantial enough to represent the user turning over or making some other large motion while sleeping. This can be determined for example by determining a vector for the motion data collected for each time period and determining a change in the angle of that vector. The described processing of information can be performed by a processor located on the device 100. The device 100 can also transmit the data for processing to a remote processor, such as a server, where processing occurs.

In some embodiments, a portion of the processing can occur on the device 100 while the remainder occurs on the remote processor.

Data is received 613 from the motion system 204 comprising data for motion in three dimensions (x, y, and z) as determined by an accelerometer or a similar motion sensor. In some embodiments, the data comprises a time dimension represented by time when the data is acquired. In some embodiments, the data is acquired periodically, for example every second, 64 times every second, 128 times every second, every 15 seconds, every 30 seconds, every 45 seconds, every 60 seconds, every 75 seconds, every 90 seconds; etc. In some embodiments, data is collected at one frequency and then averaged to provide a single data point spanning a larger time period. For example, data collected every second can be averaged to provide a single data point for each minute. Prior to further processing, a zero gravity vector is subtracted from data from each of the x, y and z directions. A vector is generated 615 from the x, y and z data associated with a particular time, e.g., each minute (or each time period t.

For each set of coordinates in three dimensions ($x_t$, $y_t$, and $z_t$) at a particular time, e.g. minute t, define a vector $\underline{A}_t := (x_t, y_t, z_t)$. An adjacent vector $\underline{B}$ at a different time, e.g. minute t+1, is given by $\underline{B}_{t+1} := (x_{t+1}, y_{t+1}, z_{t+1})$. For convenience, the time indices are omitted in the description herein. For vectors $\underline{A}$ and $\underline{B}$ that represent adjacent periods, e.g., minute t and minute t+1, a dot product 619 and a cross product 617 are calculated. The dot product and cross product are used to determine 621 the angle θ between the two adjacent vectors $\underline{A}$ and $\underline{B}$. In some embodiments, θ is calculated by the inverse tangent of (cross product)/(dot product):

$$\theta = \arctan(((\underline{A} \times \underline{B}) \cdot \underline{n})/(\underline{A} \cdot \underline{B})),$$

where "x" is a cross product of two vectors $\underline{A}$ and $\underline{B}$: $\underline{n}$ is the unit vector that is normal to a plane defined by vectors $\underline{A}$ and $\underline{B}$ and is pointing in a direction provided by the right-hand rule; and "·" is a dot product of two vectors $\underline{A}$ and $\underline{B}$.

In some embodiments, θ is calculated by using one or both of following formulas:

$$\theta = \arcsin(((\underline{A} \times \underline{B}) \cdot \underline{n})/(\|\underline{A}\|\|\underline{B}\|)) \text{ or}$$

$$\theta = \arccos(((\underline{A} \cdot \underline{B})/(\underline{A} \cdot \underline{B})/(\|\underline{A}\|\|\underline{B}\|))$$

where "x" is a cross product of two vectors $\underline{A}$ and $\underline{B}$: "·" is a dot product of two vectors $\underline{A}$ and $\underline{B}$; $\underline{n}$ is the unit vector as defined above; $\|\underline{A}\|$=magnitude of vector $\underline{A}$; and $\|\underline{B}\|$=magnitude of $\underline{B}$. In some embodiments, θ is calculated by using one or more of the above formulas, and the calculation of multiple θs is used for correcting the calculation of θ and for providing error estimation. In some embodiments, one formula is preferred over another formula to minimize the error in the calculation.

For each pair of adjacent vectors where the change in angle is greater than a threshold, the motion is identified as significant. In some embodiments, the threshold angle is set between 20 and 30 degrees, such as for example 25 degrees. In some embodiments, significant motions are classified by their magnitude. For example, motions resulting in an angle change of 20 to 35 degrees are an initial level of significant. Motions resulting in an angle change greater than 35 degrees are an increased level of significant. One of ordinary skill can add additional thresholds and levels of significance.

For a user's period of sleep, the number of significant motions is stored. In embodiments where processing of and identification of significant motions occurs on the wearable device 100, the identified significant motions can be stored locally and/or transmitted to a remote server for storage.

Combined Identification of Rem Sleep, Deep Sleep and Light Sleep

FIGS. 8A-8D illustrate a flow chart of a method of identifying and characterizing deep sleep, light sleep, and REM sleep using motion and heart rate data, according to some embodiments and being one means for performing this function of identifying different sleep stages. More specifically, the flow chart combines analyzing the motion data (changes in x-, y-, z-coordinates per second) and heart rate data (beats per minute (BPM)) to identify and characterize different sleep stages. These sleep stages include, but are not limited to deep sleep, light sleep, sleep of unknown type and REM sleep. In some embodiments, besides identifying and characterizing different sleep stages the method identifies the start and/or end times of the identified sleep stages using the motion and heart rate data. To identify stages of sleep, characteristics from either the time domain or the frequency domain are identified. In some embodiments, the method includes measuring an individual's body motion and/or heart rate during the individual's sleep activities.

Figure 15:
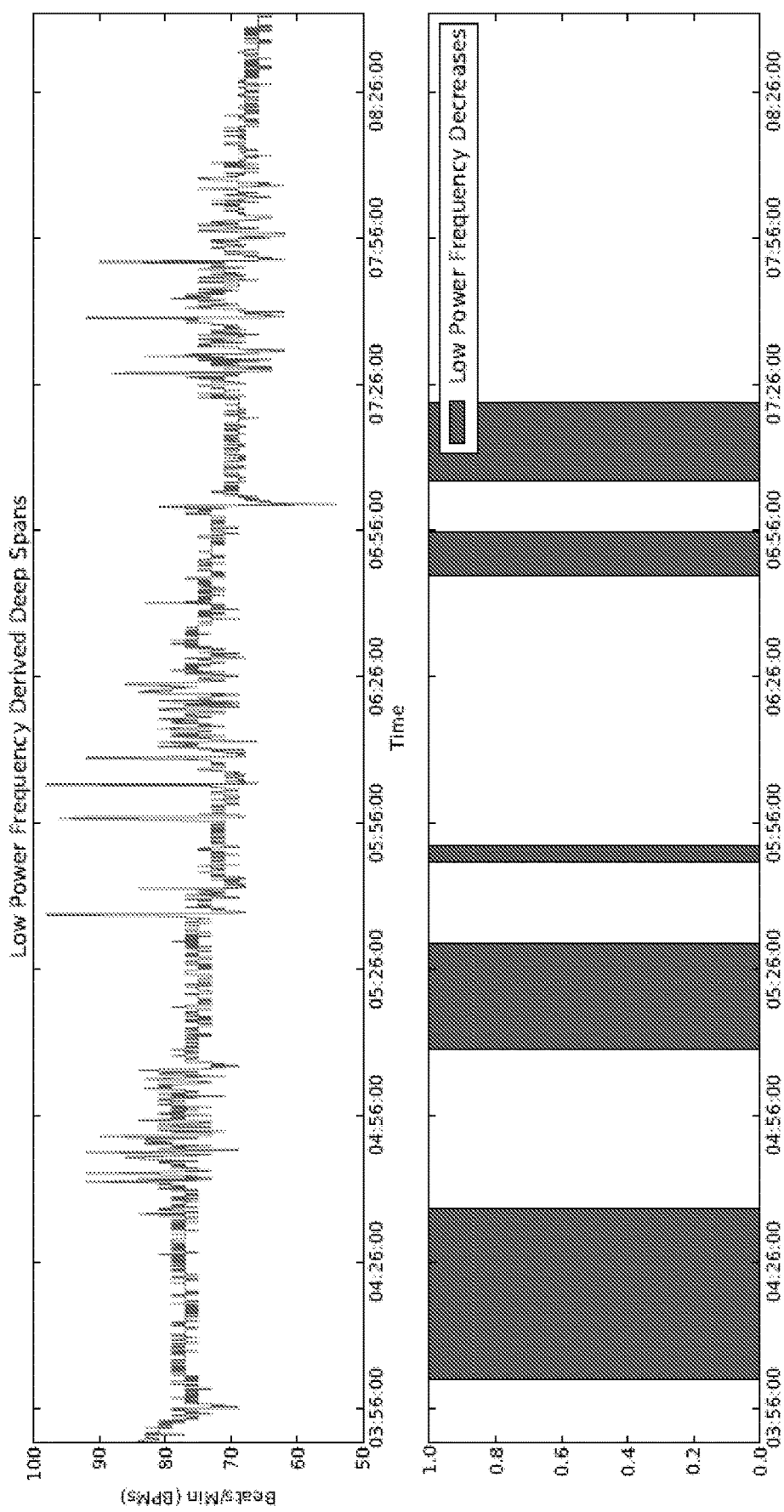
FIG. 15 illustrates determining intervals of deep sleep from identified decreases in low frequency oscillations, according to some embodiments.
Figure 16:
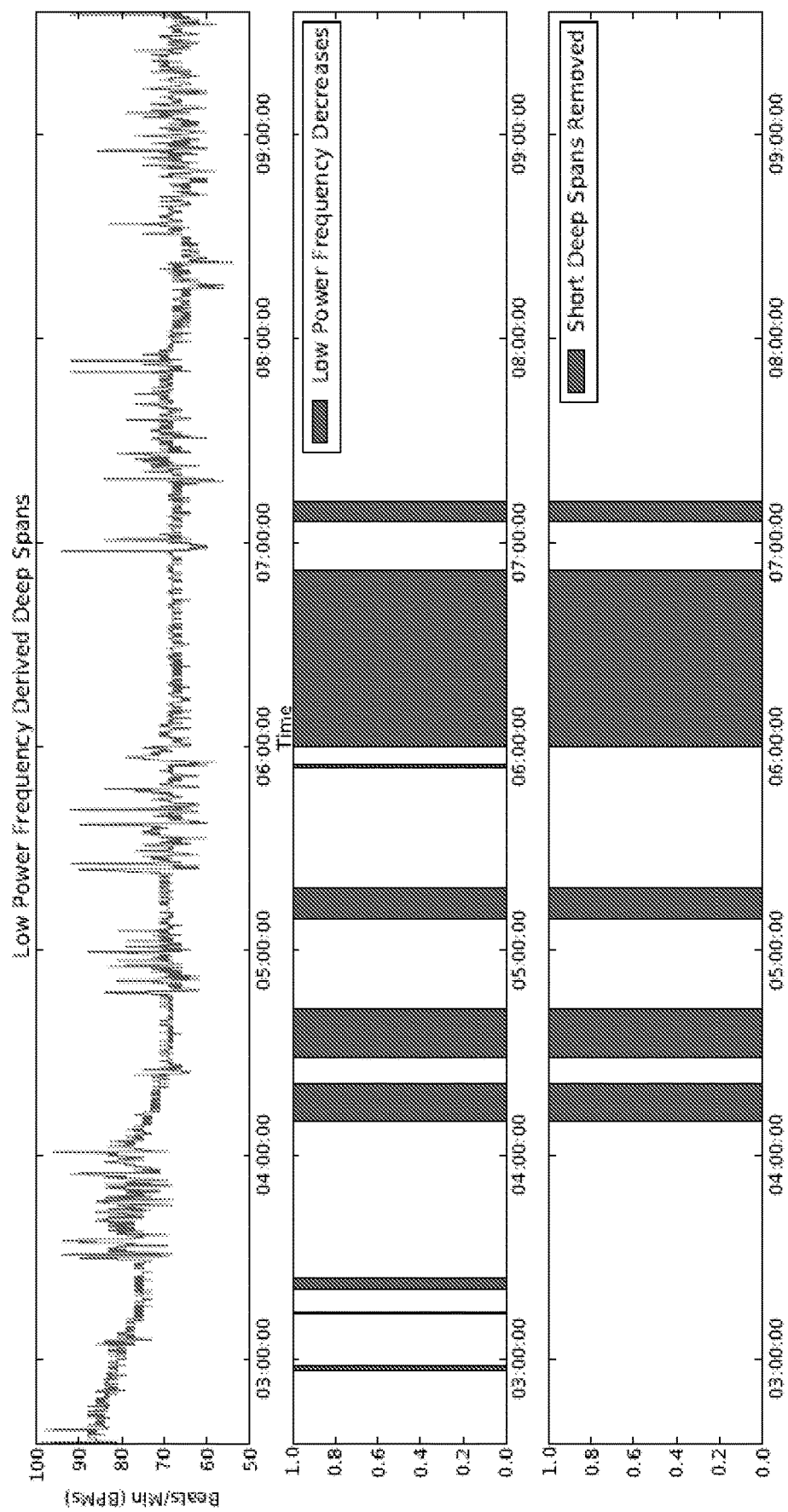
FIG. 16 illustrates determining remaining intervals of deep sleep after removal of short deep sleep intervals, according to some embodiments.

The motion data measured by for example an accelerometer is processed to determine from an individual x-, y-, and z-coordinate stream per second a magnitude root mean square (RMS) magnitude delta is computed over a window length that ranges between about 15 and about 150 seconds as described with respect to FIG. 16. In some embodiments, the window length equals 15, 30, 45, 60, 75, 90, 100, 110, 120, 125, 130, 140, or 150 seconds. In some embodiments, the motion data output is high-passed at a pre-determined threshold to filter out data artifacts. The next step comprises comparing the pre-analyzed (e.g., calculating RMS magnitude delta ("RMS-MagD")) motion data is compared to potential deep sleep spans ("Deep") that are previously identified. As illustrated in FIGS. 8A-8D, this identification comprises a first identification step ("Potential Deep Time Spans 1") based on a spectrogram analysis of the individual's heart rate. The spectrogram analysis, using smart/dynamic thresholding, identifies a spectrum and its time span to correspond to either a deep sleep ("D-Spec") or a REM sleep ("R-Spec") stage. In a second identification step ("Potential Deep Time Spans 2") the D-Spec spans are compared to REM sleep spans that are identified as described with respect to FIGS. 9-14. This comparison step is followed by a deep sleep durification and proximification step. As described with respect to FIG. 15, deep sleep durification refers to removing potential deep sleep spans that are less than or equal to a first threshold time period, 2, 3, 4 or 5 minutes Deep sleep proximification refers to combining the remaining potential deep sleep spans, which are separated from each other by less than or equal to a second threshold time period, e.g., 3, 4, 5, 6 or 7 minutes, to one continuous deep sleep span. A third identification step ("Potential Deep Time Spans 3") comprises comparing the RMS-MagD values during the durified and proximified deep sleep spans with a pre-determined RMS-MagD threshold. Any spans exceeding the RMS-MagD threshold are also removed from the deep sleep span. Applying a maximal threshold ("Deep Limiter 1") regarding the movements over a window length further removes spans from the potential deep sleep span, identifying the start and end times of a particular deep sleep span.

In some embodiments, the method identifies (characterizes) asleep stage span as an unknown type sleep span, if the heart rate gap fillers of this span equals or exceeds two minutes. The identified unknown type sleep spans are removed from further analysis to identify REM, deep or light sleep spans and determine the corresponding start and end times of those sleep spans.

In some embodiments, the method identifies a sleep span as a light sleep span, if this sleep span is not a REM sleep span, a deep sleep span or a span that is excluded from the analysis as being an unknown type sleep span. The start and end times of the light sleep span corresponds to the end and start times of the adjacent sleep spans, respectively.

In some embodiments, the method identifies a sleep span as a REM sleep span as described with respect to FIGS. 9-14. Steps of identifying REM sleep spans comprise a spectrogram analysis, standard deviation ("STD") calculation, and medium filter analysis applied to an individual's heart rate data with filling in any data portions that are missing in the acquired raw data ("Heart Rate Gaps Filler"). In some embodiments, two medium filters ("Medium Filter 1.0" and "Medium Filter 2.0"), which use smart/dynamic or dynamic thresholding, respectively, are applied to determine two filter threshold values ("Med1" and "Med2"). Following the spectrogram analysis, an R-Spec sleep span validates the STD calculation and the intersection of the STD and Med1 results in identifying "unfiltered" REM sleep spans. Similarly to deep sleep spans, the unfiltered REM sleep spans are proximified and durified followed by optionally applying one or two maximal time thresholds ("REM Limiter 1 and 2"), resulting in filtered REM sleep spans. If the filtered REM sleep spans do not fulfill the REM classification criteria as described with respect to FIG. 14, these filtered REM sleep span are identified as actual REM sleep span and their corresponding start and end times are determined. If the filtered REM sleep spans fulfill the REM classification criteria, these filtered REM sleep span are further analyzed by applying the Medium Filter 2.0, Similar to applying the Medium Filter 1.0, the R-Spec or STD of the filtered REM sleep span validates the Med2 threshold, which upon applying the Med2 threshold results in identifying actual REM sleep spans and their corresponding start and end times. In some embodiments, identifying REM sleep spans includes applying either Medium Filter 1.0 or Medium Filter 2.0, or both.

Identification of Rem Sleep

FIGS. 9-14 illustrate methods for identifying when a user is in REM sleep according to some embodiments. As a user sleeps, the device 100 collects heart rate information via the optical sensing system 205 and motion data via the motion system 204, That information is processed either by a processor located on the wearable device 100 or provided to and processed at a remotely located server.

Figure 9:
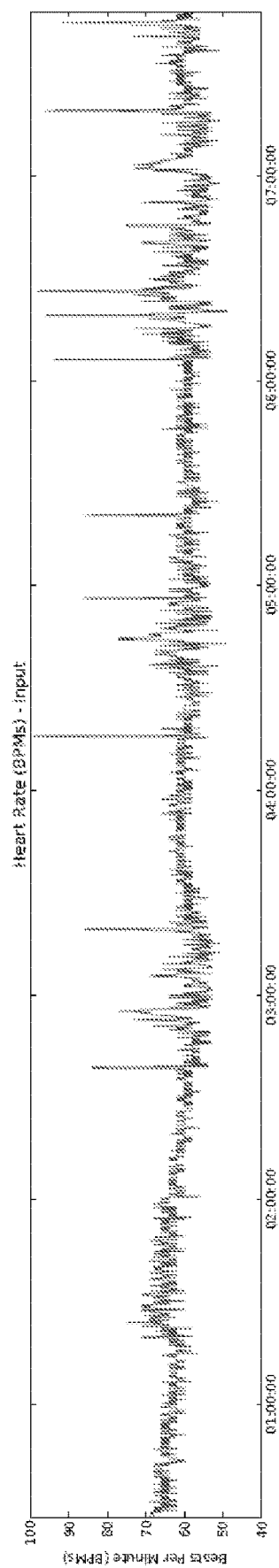
FIG. 9 shows a sample signal of a user's heart rate over an eight hour period, according to some embodiments.

FIG. 9 shows a sample signal of a user's heart rate over an eight hour period, according to some embodiments. Data output include time domain characteristics such as the standard deviation, mean and median of the heart rate, Frequency domain characteristics include the variation in low frequency oscillations. In some embodiments, portions of raw data may be missing. This can occur because the device 100 is worn and it can shift one the user's body and for a short period of time not be able to obtain data. These breaks in data can be filled in by taking the average of either data prior to the missing data, data after the missing data or a combination of both. In some embodiments, data from 10 prior and 10 post seconds are averaged and used to fill in (add) the data. The data points from before and after the missing data need not be contiguous—for example, for 10 seconds prior to the missing data, there may be more data missing and so just 10 seconds, not necessarily contiguous, can be used to fill in the first set of missing data. In some embodiments, the data that is generated to fill in missing data is stored with an identifier or tag that identifies the data as filled in data. In some embodiments, thresholds used in the method are determined using data that includes at least a threshold amount or percentage of measured as opposed to filled in data. In some embodiments, thresholds are determined with a percentage of measured data that is 90% or greater. In some embodiments, spans exceeding a threshold amount of filled in data, for example two minutes or longer, are not considered for identifying a sleep stage or type. A span refers to a period or interval of time (interrupted or uninterrupted) when data is acquired or missing data is filled in, i.e. added to, at times when no data has been acquired. A span can also refer to a set of frequencies corresponding to a time period or interval upon applying a time-frequency transformation. The filled in data is used to provide continuity to the remainder of the data so that there are no artificial features included in the method due to missing data or gaps in the acquired data. For example, missing data can look like a sudden decrease in heart rate in the signal, when in fact the lack of data can be attributed to no data being acquired for a particular time period. In turn, this can affect the extraction of sleep features based on a measurement artifact. Thus, filling in data is useful even if the actual time periods of filled in data are not used to identify (classify) a sleep stage or type.

In some embodiments, the signal in the range of 0-0.4 Hz; 0.03-0.05 Hz; 0.05-0.13 Hz; 0.04-0.15 Hz; 0.13-0.4 Hz; 0.03-0.08 Hz; or 0.10-0.18 Hz is analyzed to identify increases in low frequency oscillations. In some embodiments, the length of a Fast Fourier Transform (FFT) applied to these frequency ranges is kept constant at 256 samples, while also considering frequency overlaps. A threshold is computed using a combination of average low frequency power, low power frequency variance, and a low frequency multiplier.

Figure 10:
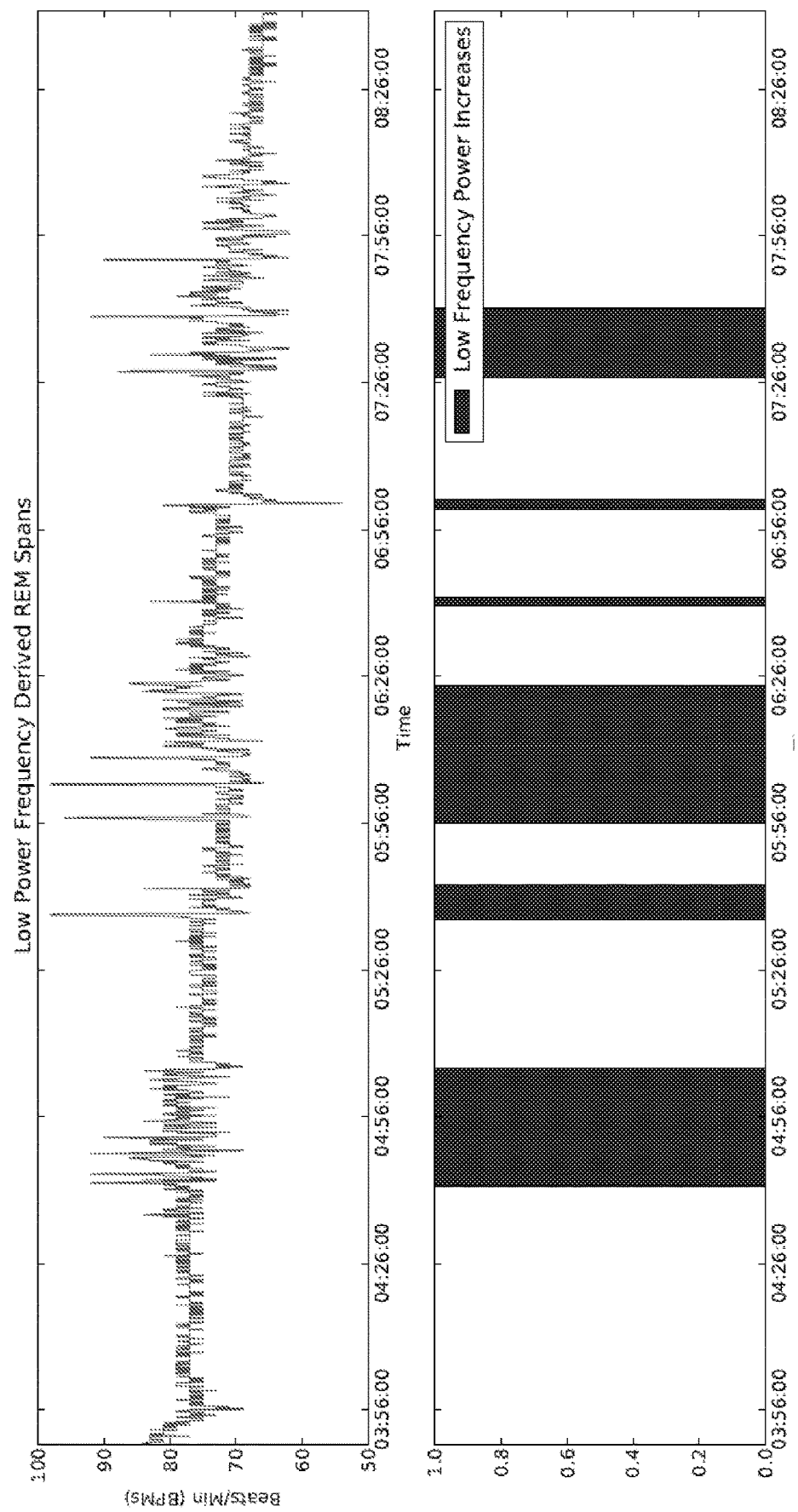
FIG. 10 illustrates a raw signal of a user's heart rate identifying love frequency power increases, according to some embodiments.

FIG. 10 illustrates the portions of the signal that meet these criteria when the analyzed frequency is 0.05-0.13 Hz, according to some embodiments. Standard deviation changes are determined across the heart rate signal using windows of time, also referred to as epochs. Epochs can be any length such as 15, 30, 45, 60, 75, or 90 seconds. In one embodiment, a variance is computed for every 30 second epoch. Increases in standard deviation changes are identified and the threshold is computed using a combination of average variance, variance of standard deviation throughout epochs, and a standard deviation threshold multiplier.

Figure 11:
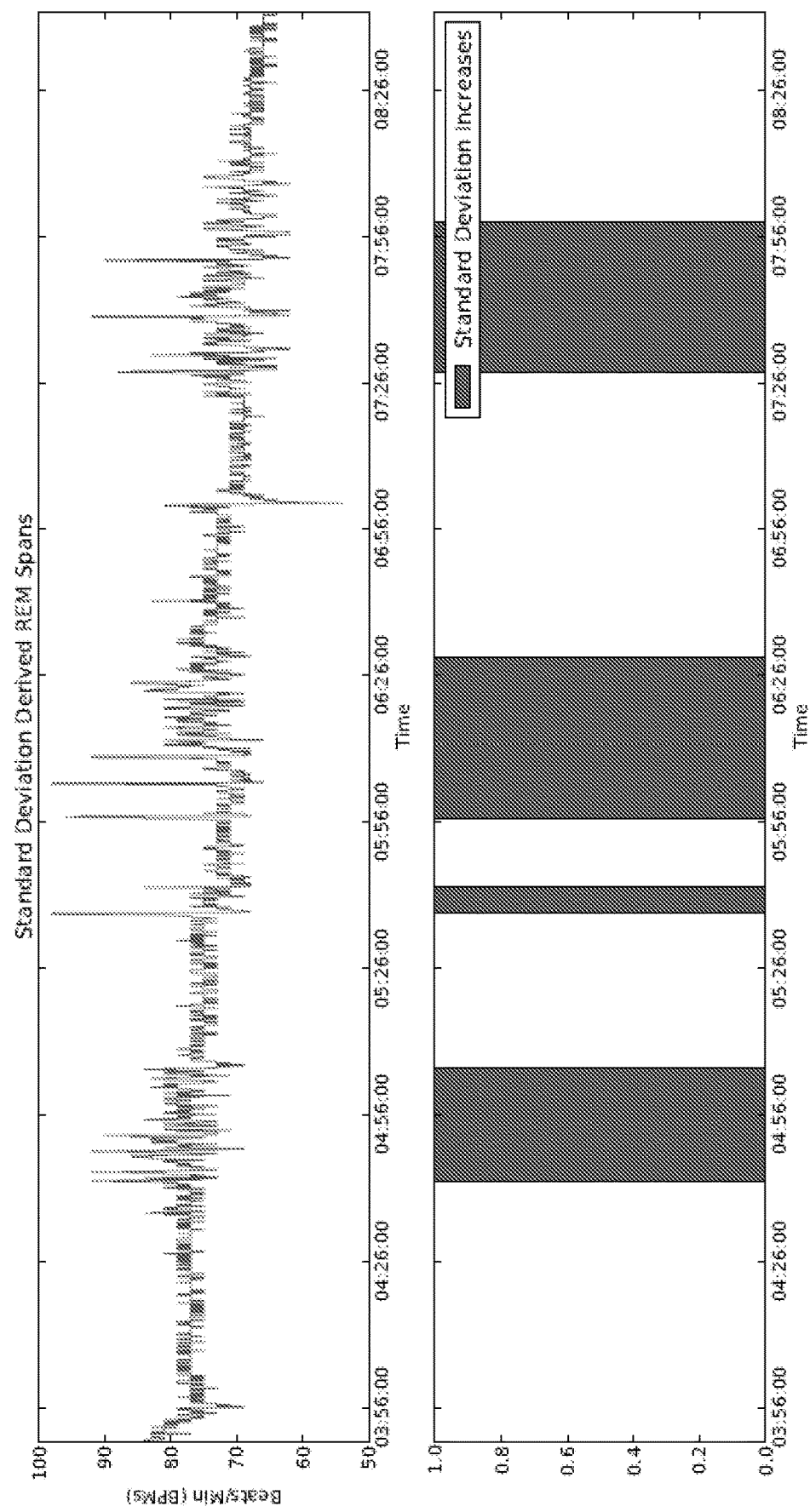
FIG. 11 illustrates a raw signal of heart rate identifying time periods where there the variance in standard deviation exceeds a threshold, according to some embodiments.

FIG. 11 illustrates the portions of the signal that meet these criteria, according to some embodiments. A median filter of a predetermined length, of for example 301 samples, is computed for the heart rate signal. In some embodiments, other sample lengths are used that are known to a person skilled in the art. In some embodiments, at least 90% of the data used to determine the median in a window needs to be acquired (real) data, as opposed to filled in data. The median is determined for each 301 sample window in the data. Increases in heart rate without any artifacts or spikes are identified and a threshold is computed using an average post filter and/or a variance post filter.

Figure 12:
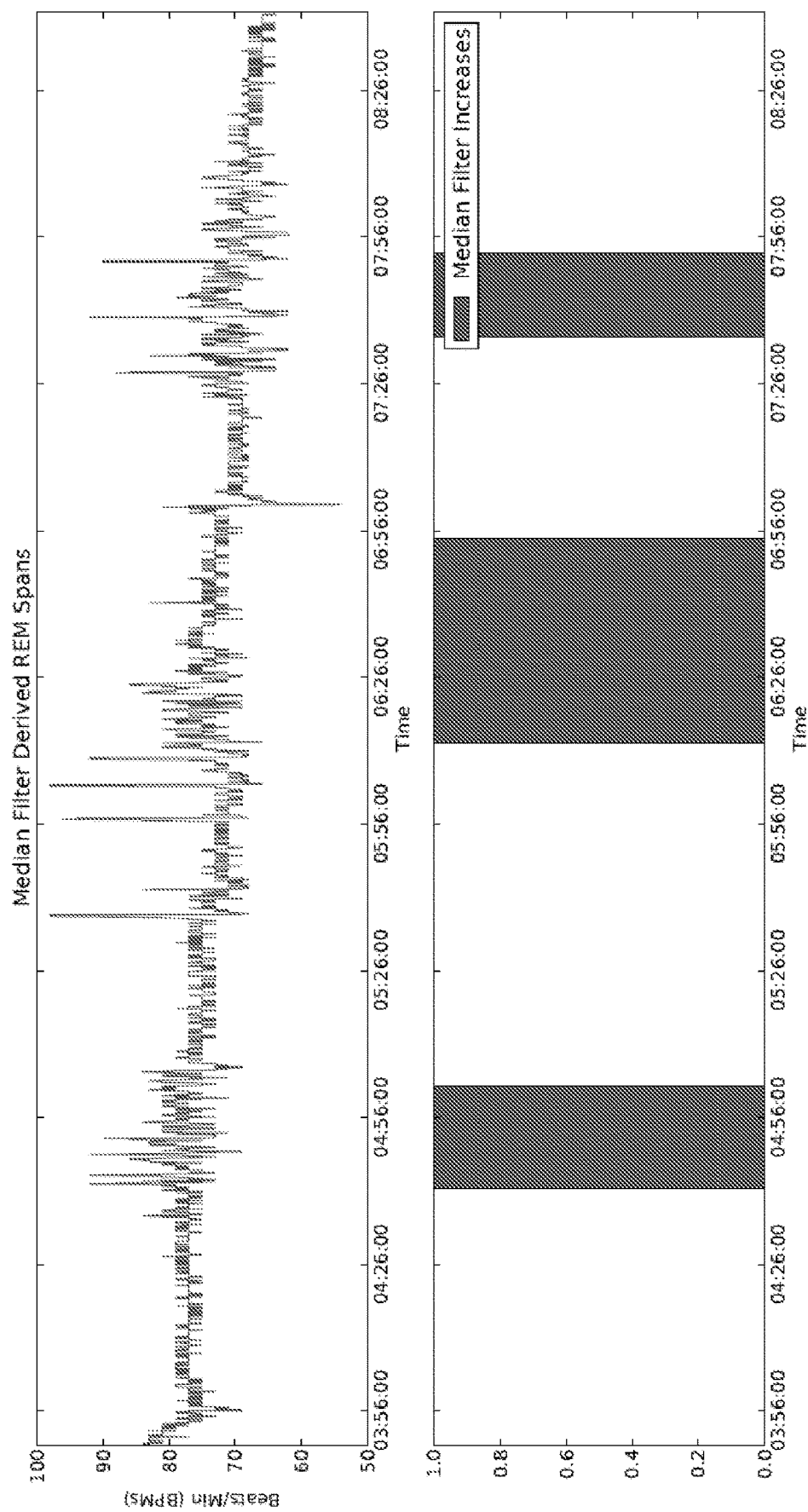
FIG. 12 illustrates a raw signal of heart rate identifying time periods where the signal does meets the criteria of the median filter, according to some embodiments.
Figure 13:
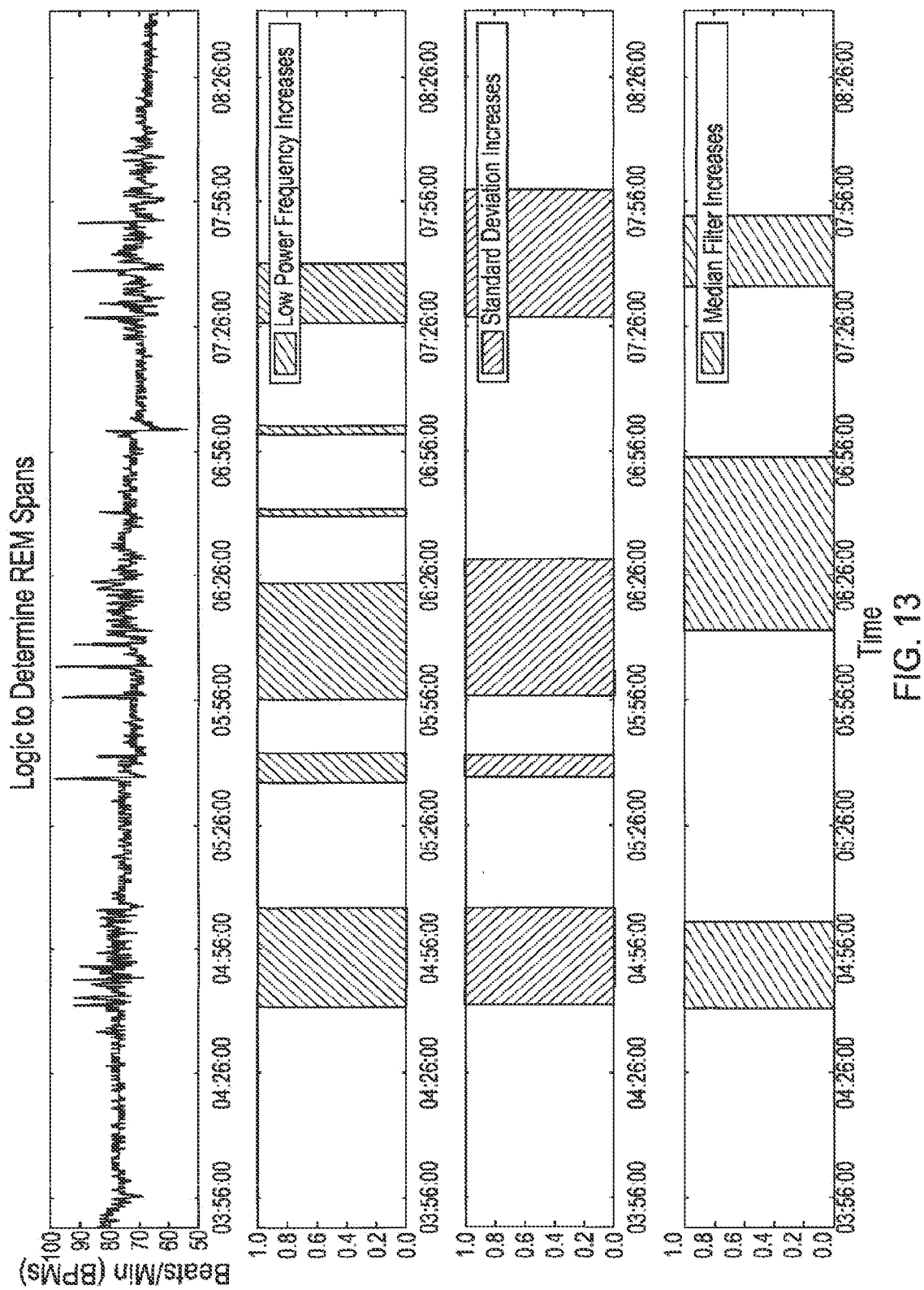
FIG. 13 illustrates a raw signal of heart rate as well as time periods that meet the criteria previously shown in FIGS. 10-12, according to some embodiments.

FIG. 12 illustrates the portions of a signal that meet these criteria, according to some embodiments, and FIG. 13 further illustrate standard deviation increases that are mapped out as spans with start and end times, according to some embodiments. If these standard deviations spans contain increases in low frequency oscillations or if these standard deviation spans overlap with increases in mean heart rate derived from the median filter, then these are identified as potential REM time spans. In some embodiments, the standard deviation span overlaps for one second with an increase in low frequency oscillations to identify the span as a potential REM span. In some embodiments, a span is identified as a potential REM span if the standard deviation span overlaps the spans created by the increase in mean heart rate derived from the median filter.

Referring back to FIG. 13, in some embodiments, the potential REM spans are combined if they occur within a threshold amount of time of each other. In some embodiments, that threshold is nine minutes. In some embodiments, potential REM spans that are less than a threshold length, for example two minutes, in duration are removed from potential REM spans. Similarly, potential REM spans that are longer than a threshold amount of time, for example, one hour, are also removed from potential REM spans, because a person would not likely remain in a single span of REM sleep for such a long time span. Optionally, any potential REM spans that occur within an initial threshold amount of time, for example twenty minutes, after onset of sleep are also removed from potential REM spans. Because the heart rate is naturally slowing down as a person falls asleep, this change in the heart rate mimics the onset of REM sleep and can lead to false positive identification of REM sleep. Spans removed as potential REM spans may be identified as deep sleep or light sleep by further analysis.

Figure 14:
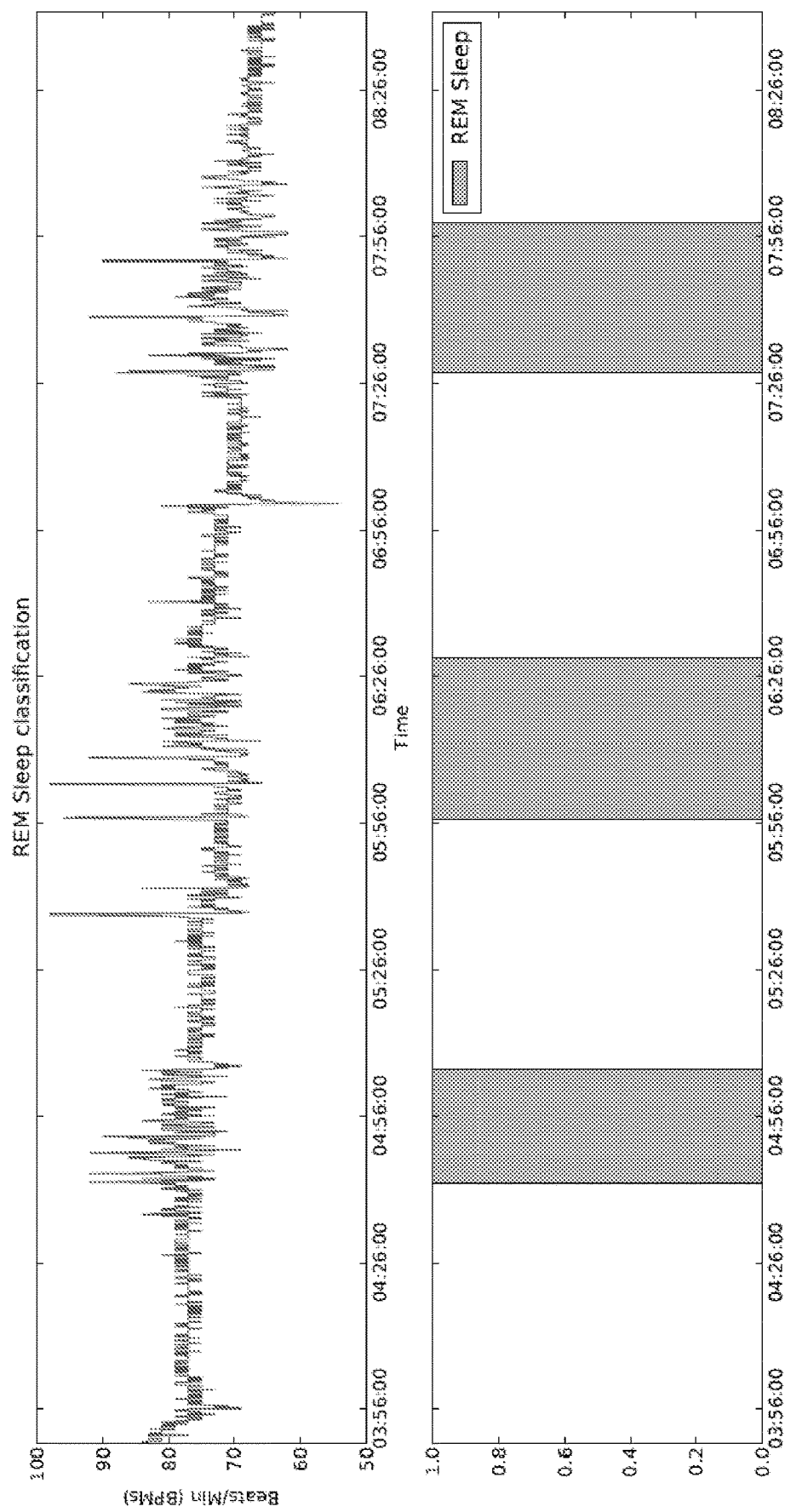
FIG. 14 illustrates determining intervals of REM sleep, according to some embodiments.

FIG. 14 illustrates the potential REM spans, which remain after the described processing, are identified as REM spans, according to some embodiments. In some embodiments, REM spans can be identified using just changes in standard deviation of the heart rate. Optionally, the REM spans are identified using changes in standard deviation of heart rate and the median heart rate filter. Thus, in some embodiments, REM sleep is identified using just time domain characteristics of the heart rate data.

For some users, the described processing does not identify all of the REM spans of this user's sleep stages. For example, the heart rate of some users does not vary significantly, and the heart rate's standard deviation does therefore not exceed a pre-determined threshold. In such cases, it is difficult to identify high variability regions. Instead, in some embodiments, mean increases are identified and a threshold is calculated using a combination of an average and variance of a down sampled, smoothed, and detrended heart rate signal. If a user's data meets certain criteria, additional processing is implemented to complete the identification of REM spans. In some embodiments, these criteria include: 1) REM spans identified in a first processing account for less than a threshold percentage (e.g., a threshold percentage that is less than or equal to 19%) of the sleep time; and 2) a filtered standard deviation is less than a threshold (e.g., a standard deviation that is less than or equal to 2). In some embodiments, additional processing is triggered by one or both of the above criteria being met. During shorter periods of sleep, such as a nap, REM sleep is less likely to follow planned or pre-determined patters, such as a percentage amount of sleep being REM sleep compared to light or deep sleep. Thus, in some embodiments, additional processing of the data is triggered when one or more of the above criteria are met and the total sleep time was longer than a threshold (e.g., the total sleep time is larger than or equal to 3.5 hours).

Additional processing comprises down sampling the heart rate signal with a 60 second average, and optionally smoothing the down-sampled signal with a Gaussian filter. In some embodiments, a least squares approximation is used to detrend the smoothed and down-sampled signal. In some embodiments, increases in low frequency power oscillations or in standard deviation are typically present in time spans that have undergone additional processing, and are identified as time spans of REM sleep.

Identification of Deep Sleep

Referring to FIGS. 15-18, a method for the identification of deep sleep is described, according to some embodiments. In this method the heart rate signal is analyzed to identify decreases in low frequency oscillations. A threshold is computed using a combination of average low frequency power, low power frequency variance, and a low frequency multiplier. In some embodiments, a historical overlap is introduced in the threshold calculation, which looks back ten minutes to analyze changes in low frequency power of the heart rate. Those periods of time, where the decreases in low frequency oscillations exceed the calculated threshold are identified as potential spans of deep sleep. Potential deep sleep time spans obtained from the frequency analysis are removed if these deep sleep time spans overlap with REM sleep spans that for example have been identified as described above. This step of removing deep sleep spans overlapping with REM sleep spans ensures that REM and deep sleep time spans are independent from each other.

FIG. 15 illustrates potential spans of deep sleep, according to some embodiments Potential deep sleep spans (segments) less than or equal to a first threshold time period, for example 2, 3, 4 or 5 minutes, are removed, and the remaining potential deep sleep spans that are separated from each other by less than or equal to a second threshold time period, for example 3, 4, 5, 6 or 7 minutes, are combined to one continuous deep sleep span.

FIG. 16 shows the potential spans of deep sleep after this additional analysis, according to some embodiments. Data from the motion system 204 is analyzed. In some embodiments, where the motion system 204 is a three-axis accelerometer, a zero gravity vector is subtracted from each individual y-, and z-coordinate stream before a magnitude root mean square (RMS) is calculated. In some embodiments, an exponential moving average is computed for a set of motion data. In some embodiments, an accelerometer RMS magnitude delta is computed over a window length that ranges between about 15 and about 150 seconds. In some embodiments, the window length equals 15, 30, 45, 60, 75, 90, 100, 110, 120, 125, 130, 140, or 150 seconds. In some embodiments, the motion data output is high-passed at a pre-determined threshold to filter out data artifacts.

In some embodiments, the motion data, which is optionally pre-analyzed as described above, is compared to potential deep sleep spans. Potential deep sleep spans, during which more than a threshold number of filtered movements occur, e.g., more than four movements, are removed as potential deep sleep spans, because the brain inhibits a person's motion during periods of the person being in deep sleep. Thus, motion is unlikely to occur to any significant extent, e.g., more than four movements over the window length, while a person is in deep sleep.

Figure 17:
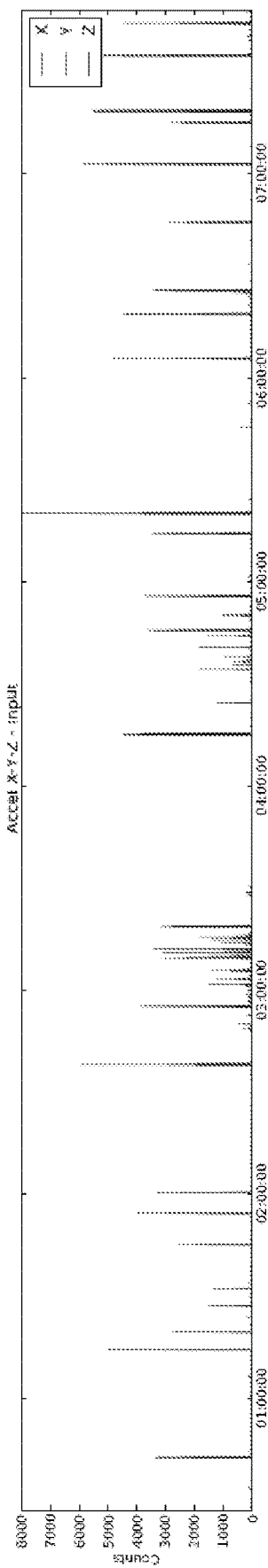
FIG. 17 illustrates exemplary motion data during the user's sleep, according to some embodiments.
Figure 18:
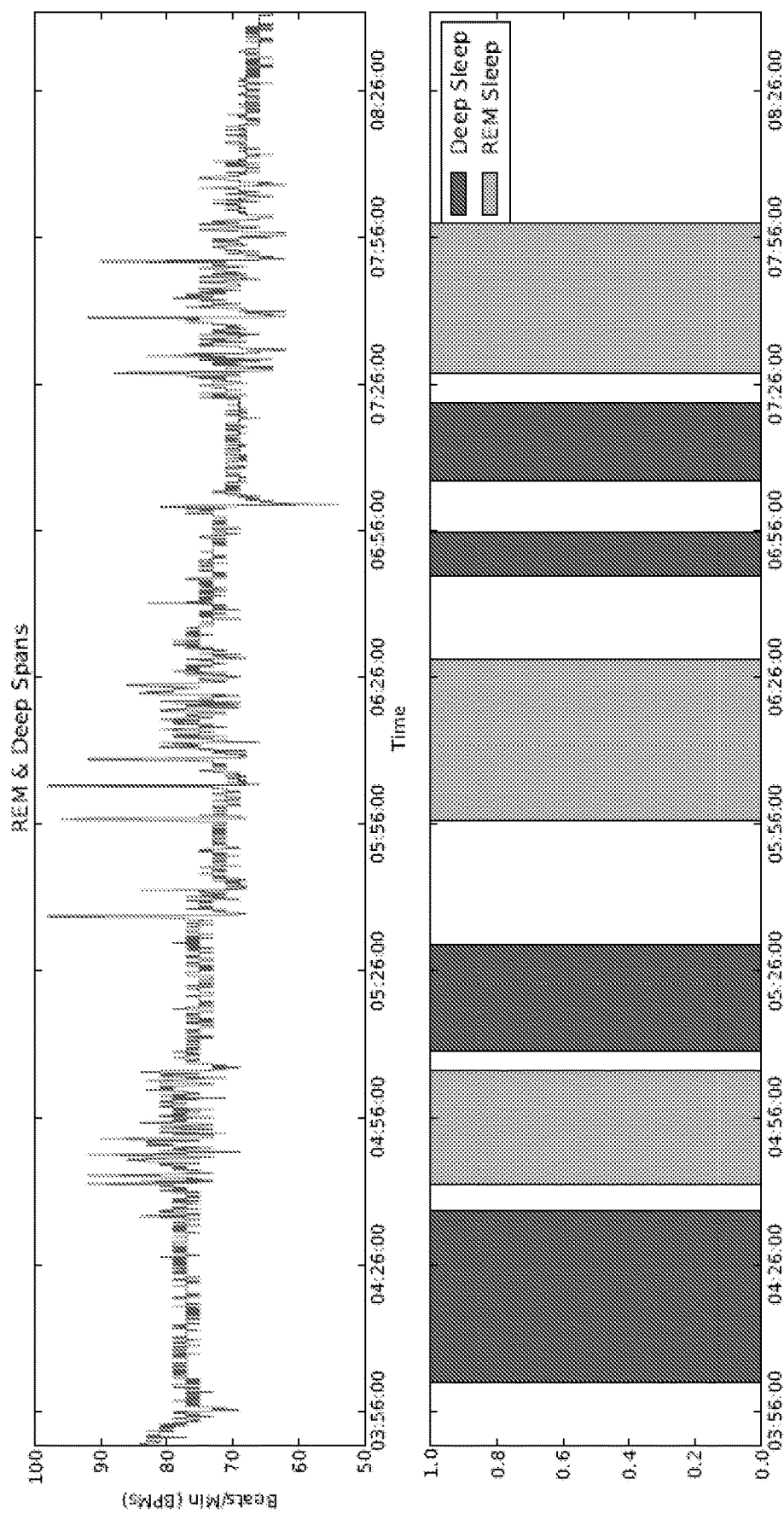
FIG. 18 illustrates determining intervals of REM and deep sleep, according to some embodiments.

FIG. 17 illustrates exemplary motion data during the user's sleep, according to some embodiments, and FIG. 18 further illustrates the user's night of sleep with deep and REM spans of sleep identified, according to some embodiments. Those portions of sleep not identified as either deep or REM sleep are identified as light sleep. In some embodiments, a user's history of REM and deep sleep is stored, for example at a remote server. The processing of a user's sleep to identify various stages of sleep can then be personalized based on the stored information. Processing of a user's sleep can further be personalized through information about a user's location (i.e., weather conditions, sound-generating events, obtainable via, for example, the internet), ambient light (available through the optical system 205), ambient temperature (in embodiments where the device 100 further comprises a temperature sensor).

Computer System

Figure 19:
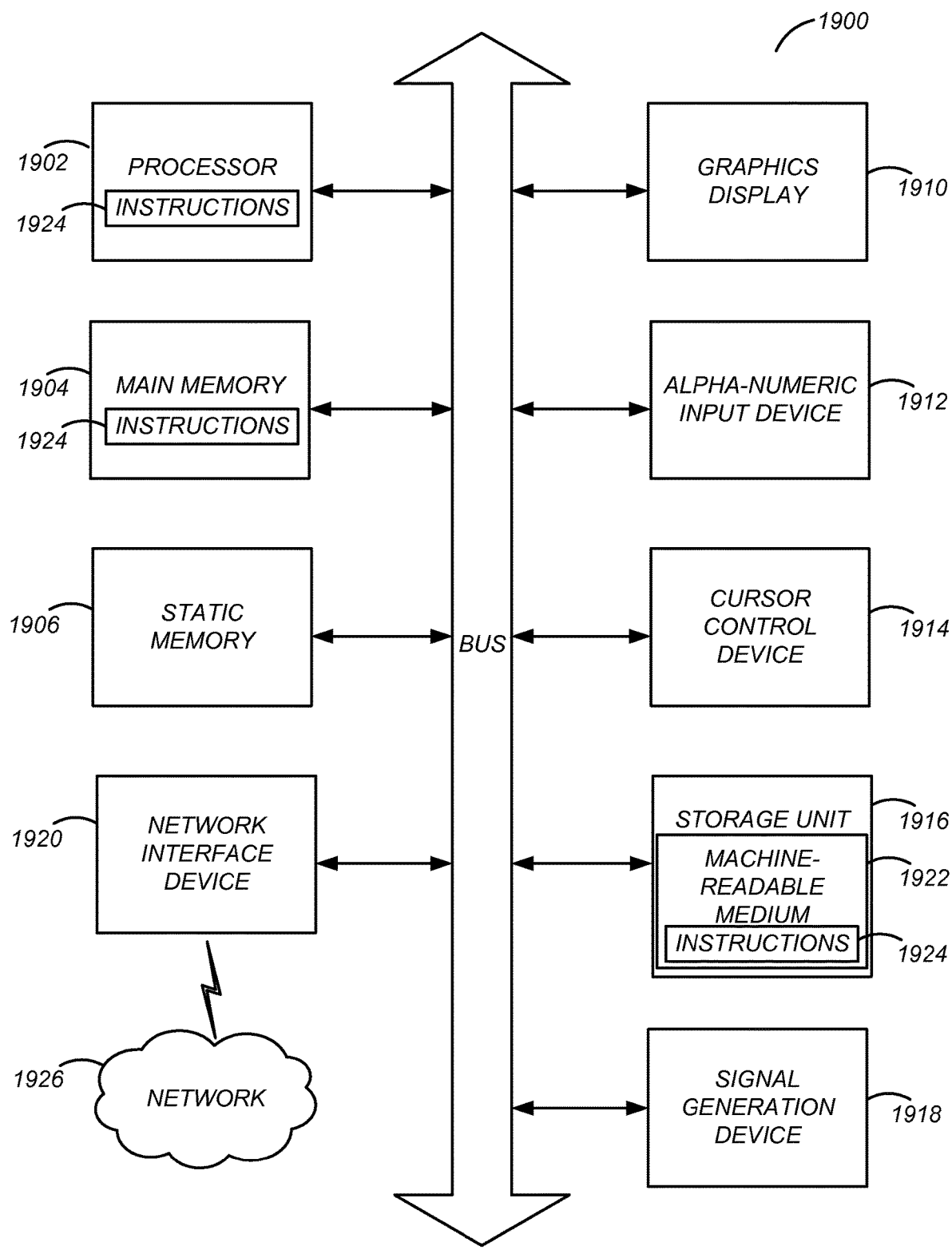
FIG. 19 is a block diagram illustrating components of a machine able to read instructions from a machine-readable medium and execute them in a processor, according to some embodiments.

FIG. 19 is a block diagram illustrating components of a machine able to read instructions from a machine-readable medium and execute them in a processor (or controller). In some embodiments, the wearable device 100 comprises such a machine. In some embodiments, the wearable device 100 is in communication with such a machine that is remote and separate from the wearable device. Specifically, FIG. 19 shows a diagrammatic representation of such a machine in the form of a computer system 1900 within which instructions 1924 (e.g., software) for causing the machine to perform any one or more of the methodologies discussed herein may be executed. The computer system 1900 may be used to perform operations associated with designing a test circuit including a plurality of test core circuits arranged in a hierarchical manner.

In some embodiments, the computer system 1900 includes a processor 1902 (e.g., a central processing unit (CPU), a graphics processing unit (GPU), a digital signal processor (DSP), one or more application specific integrated circuits (ASICs), one or more radio-frequency integrated circuits (RFTCs), or any combination of these), a main memory 1904, and a static memory 1906, which are configured to communicate with each other via a bus 1908. The computer system 1900 may further include graphics display unit 1910 (e.g., a plasma display panel (PDP), a liquid crystal display (LCD), a projector, or a cathode ray tube (CRT)). The computer system 1900 may also include alphanumeric input device 1912 (e.g., a keyboard), a cursor control device 1914 (e.g., a mouse, a trackball, a joystick, a motion sensor, or other pointing instrument), a storage unit 1916, a signal generation device 1918 (e.g., a speaker), and a network interface device 1920, which also are configured to communicate via the bus 1908.

The storage unit 1916 includes a machine-readable medium 1922 on which is stored instructions 1924 (e.g., software) embodying any one or more of the methodologies or functions described herein. The instructions 1924 (e.g., software) may also reside, completely or at least partially, within the main memory 1904 or within the processor 1902 (e.g., within a processor's cache memory) during execution thereof by the computer system 1900, the min memory 1904 and the processor 1902 also constituting machine-readable media. The instructions 1924 (e.g., software) may be transmitted or received over a network 1926 via the network interface device 1920. The machine-readable medium 1922 may also store a digital representation of a design of a test circuit.

While machine-readable medium 1922 is shown in an example embodiment to be a single medium, the term "machine-readable medium" should be taken to include a single medium or multiple media (e.g., a centralized or distributed database, or associated caches and servers) able to store instructions (e.g., instructions 1924). The term "machine-readable medium" shall also be taken to include any medium that is capable of storing instructions instructions 1924) for execution by the machine and that cause the machine to perform any one or more of the methodologies disclosed herein. The term "machine-readable medium" includes, but not be limited to, data repositories in the form of solid-state memories, optical media, and magnetic media.

ADDITIONAL CONSIDERATIONS

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

The optical sensing system 205 of the device 100 can be used to augment the information provided to the user about activity during sleep. For example, heart rate data can be determined from the optical data and this can be combined with the motion information either in combination—by providing a user analysis of heart rate next to motion data. Additionally or alternatively, the heart rate data can be used as further input to identify which movements are significant. The optical sensing system 205 can further provide information about ambient light while the user is sleeping. Like heart rate data, this can be presented alongside motion data or used to identify which motion is significant. The device can include other sensors, including, for example, an ambient temperature sensor which can be further used to enhance analysis of a user's sleep. Like heart rate data, temperature can be presented alongside motion data or used to identify which motion is significant.

In some embodiments, the significant motions are displayed to a user as a total number of motions. Alternatively or additionally, a graphical representation of the user's significant motions is provided. For example, a timeline of the user's sleep time is provided showing where each significant motion occurred in time. This can be shown in combination with other information about the user during this time period. For example, if device 100 includes modules for the collection of other data, such as heart rate, heart rate data and information derived from heart rate data can also be displayed.

Certain embodiments are described herein as including logic or a number of components, modules, or mechanisms. For example, the functions corresponding to the process steps in FIGS. 6-8 may be embodied as discrete modules (e.g., one for each function). Modules may constitute either software modules (e.g., program code (or instructions) embodied on a machine-readable medium) or hardware modules. A hardware module is tangible unit capable of performing certain operations and may be configured or arranged in a certain manner. In example embodiments, one or more computer systems (e.g., a standalone, client or server computer system) or one or more hardware modules of a computer system (e.g., processor 203) may be configured by software (e.g., an application or application portion) as a hardware module that operates to perform certain operations as described herein.

The various operations of example methods described herein, e.g., those methods illustrated in FIGS. 6-8, may be performed, at least partially, by one or more processors, e.g., 203, that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

In various embodiments, a hardware module may be implemented mechanically or electronically. For example, a hardware module may comprise dedicated circuitry or logic that is permanently configured (e.g., as a special-purpose processor, such as a field programmable gate array (FPGA) or an application-specific integrated circuit (ASIC)) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Some portions of above description describe the embodiments in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like. Furthermore, it has also proven convenient at times, to refer to these arrangements of operations as modules, without loss of generality. The described operations and their associated modules may be embodied in software, firmware, hardware, or any combinations thereof.

The features and advantages described in the specification are not all inclusive and, in particular, many additional features and advantages will be apparent to one of ordinary skill in the art in view of the drawings, specification, and claims. Moreover, it should be noted that the language used in the specification has been principally selected for readability and instructional purposes, and may not have been selected to delineate or circumscribe the disclosed subject matter.

The one or more processors may also operate to support performance of the relevant operations in a "cloud computing" environment or as a "software as a service" (SaaS). For example, at least some of the operations may be performed by a group of computers (as examples of machines including processors), these operations being accessible via a network (e.g., the Internet) and via one or more appropriate interfaces (e.g., application program interfaces (APIs).)

The performance of certain of the operations may be distributed among the one or more processors, not only residing within a single machine, but deployed across a number of machines. In some example embodiments, the one or more processors or processor-implemented modules may be located in a single geographic location (e.g., within a home environment, an office environment, or a server farm). In other example embodiments, the one or more processors or processor-implemented modules may be distributed across a number of geographic locations.

Some portions of this specification are presented in terms of algorithms or symbolic representations of operations on data stored as bits or binary digital signals within a machine memory (e.g., a computer memory). These algorithms or symbolic representations are examples of techniques used by those of ordinary skill in the data processing arts to convey the substance of their work to others skilled in the art. As used herein, an "algorithm" is a self-consistent sequence of operations or similar processing leading to a desired result. In this context, algorithms and operations involve physical manipulation of physical quantities. Typically, but not necessarily, such quantities may take the form of electrical, magnetic, or optical signals capable of being stored, accessed, transferred, combined, compared, or otherwise manipulated by a machine. It is convenient at times, principally for reasons of common usage, to refer to such signals using words such as "data," "content," "bits," "values," "elements," "symbols," "characters," "terms," "numbers," "numerals," or the like. These words, however, are merely convenient labels and are to be associated with appropriate physical quantities.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. It should be understood that these terms are not intended as synonyms for each other. For example, some embodiments may be described using the term "connected" to indicate that two or more elements are in direct physical or electrical contact with each other. In another example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the invention. This description should be read to include one or at least one and the singular also includes the plural unless it is obvious that it is meant otherwise.

Upon reading this disclosure, those of skill in the art will appreciate still additional alternative structural and functional designs for a system and a process for identification and characterization of nocturnal motion and/or sleep stages through the disclosed principles herein. Thus, while particular embodiments and applications have been illustrated and described, it is to be understood that the disclosed embodiments are not limited to the precise construction and components disclosed herein. Various modifications, changes and variations, which will be apparent to those persons skilled in the art, may be made in the arrangement, operation and details of the method and apparatus disclosed herein without departing from the spirit and scope defined in the appended claims.

The invention claimed is:

1. A method for identifying rapid eye movement (REM) sleep, the method comprising:
   receiving heart rate data associated with a sleeping user at a plurality of time points;
   identifying a first time domain characteristic of the heart rate data, wherein identifying the first time domain characteristic of heart rate data comprises analyzing changes in a standard deviation of heart rate in the heart rate data and determining a first time span based on the analyzed changes in the standard deviation of heart rate for the first time domain characteristic;
   identifying a second time domain characteristic of the heart rate data, wherein identifying the second time domain characteristic of heart rate data comprises determining a median heart rate for the plurality of time points, analyzing changes in the median heart rate of the heart rate data, and determining a second time span based on the analyzed changes in the median heart rate for the second time domain characteristic; and
   determining a presence of REM sleep based on an overlap of the first and second time spans for the identified first and second time domain characteristics of the heart rate data.

2. The method of claim 1, wherein the changes in the standard deviation of heart rate in the heart rate data comprise an increase in the standard deviation of heart rate, and wherein the changes in the median heart rate of the heart rate data comprise an increase in the median heart rate.

3. The method of claim 1 further comprising:
   identifying a frequency domain characteristic of the heart rate data, analyzing changes in the frequency domain characteristic, and determining a third time span based on the analyzed changes in the frequency domain characteristic; and
   determining the presence of REM sleep is further based on an overlap of the first, the second, and the third time spans for the identified first and second time domain characteristics and the identified frequency domain characteristic of the heart rate data.

4. The method of claim 3, wherein the frequency domain characteristic comprises a change in low frequency oscillation.

5. The method of claim 4, wherein the change in low frequency oscillation comprises an increase in low frequency oscillations.

6. The method of claim 1, wherein receiving the heart rate data comprises receiving data from an optical sensor.

7. The method of claim 6, wherein the data from the optical sensor comprises data indicating an amount of light absorbed by tissue of the user.

8. A system for identifying rapid eye movement (REM) sleep, the system comprising:
   a memory element configured to store data;
   a processor operable to execute instructions associated with the data; and
   a module configured to:
      receive heart rate data associated with a sleeping user at a plurality of time points;
      identify a first time domain characteristic of the heart rate data, wherein identifying the first time domain characteristic of heart rate data comprises analyzing changes in a standard deviation of heart rate in the heart rate data and determining a first time span based on the analyzed changes in the standard deviation of heart rate for the first time domain characteristic;
      identify a second time domain characteristic of the heart rate data, wherein identifying the second time domain characteristic of heart rate data comprises determining a median heart rate for the plurality of time points, analyzing changes in the median heart rate of the heart rate data, and determining a second time span based on the analyzed changes in the median heart rate for the second time domain characteristic; and
      determine a presence of REM sleep based on an overlap of the first and second time spans for the identified first and second time domain characteristics of the heart rate data.

9. The system of claim 8, wherein the changes in the standard deviation of heart rate in the heart rate data comprise an increase in the standard deviation of heart rate, and wherein the changes in the median heart rate of the heart rate data comprise an increase in the median heart rate.

10. The system of claim 8, wherein the module is further configured to identify a frequency domain characteristic of the heart rate data, analyze changes in the frequency domain characteristic, and determine a third time span based on the analyzed changes to the frequency domain characteristic; and determine the presence of REM sleep is further based on an overlap of the first, the second, and the third time spans for the identified first and second time domain characteristics and the identified frequency domain characteristic of the heart rate data.

11. The system of claim 10, wherein the changes in the standard deviation of heart rate in the heart rate data comprise an increase in the standard deviation of heart rate, and wherein the frequency domain characteristic comprises a change in low frequency oscillation.

12. The system of claim 11, wherein the change in low frequency oscillation comprises an increase in low frequency oscillations.

13. The system of claim 8, wherein receiving the heart rate data comprises receiving data from an optical sensor.

14. The system of claim 13, wherein the data from the optical sensor comprises data indicating an amount of light absorbed by tissue of the user.

15. One or more non-transitory tangible media that includes code for execution and when executed by a processor is operable to perform operations comprising:
   receiving heart rate data associated with a sleeping user at a plurality of time points;
   identifying a first time domain characteristic of the heart rate data, wherein identifying the first time domain characteristic of heart rate data comprises analyzing changes in a standard deviation of heart rate in the heart rate data and determining a first time span based on the analyzed changes in the standard deviation of heart rate for the first time domain characteristic;
   identifying a second time domain characteristic of the heart rate data, wherein identifying the second time domain characteristic of heart rate data comprises determining a median heart rate for the plurality of time points, analyzing changes in the median heart rate of the heart rate data, and determining a second time span based on the analyzed changes in the median heart rate for the second time domain characteristic; and determining a presence of rapid eye movement (REM) sleep based on an overlap of the first and second time spans for the identified first and second time domain characteristics of the heart rate data.

16. The media of claim 15, wherein the changes in the standard deviation of heart rate in the heart rate data comprise an increase in the standard deviation of heart rate, and wherein the changes in the median heart rate of the heart rate data comprise an increase in the median heart rate.

17. The media of claim 15, wherein the operations further comprise identifying a frequency domain characteristic of the heart rate data, analyzing changes in the frequency domain characteristic, and determining a third time span based on the analyzed changes in the frequency domain characteristic; and determining the presence of REM sleep is further based on an overlap of the first, the second, and the third time spans for the identified first and second time domain characteristics and the identified frequency domain characteristic of the heart rate data.

18. The media of claim 17, wherein the frequency domain characteristic comprises a change in low frequency oscillation.

* * * * *